United States Patent [19]

Altman

[11] Patent Number: 5,551,427
[45] Date of Patent: Sep. 3, 1996

[54] IMPLANTABLE DEVICE FOR THE EFFECTIVE ELIMINATION OF CARDIAC ARRHYTHMOGENIC SITES

[76] Inventor: Peter A. Altman, 370 Altair Way Suite 302, Sunnyvale, Calif. 94086

[21] Appl. No.: 387,257

[22] Filed: Feb. 13, 1995

[51] Int. Cl.⁶ .................................................. A61N 1/05
[52] U.S. Cl. .................. 128/642; 607/120; 607/121; 607/122; 607/126; 607/127; 607/128
[58] Field of Search .................. 128/642; 607/120–127, 607/119, 131, 37, 60, 1, 2

[56] References Cited

U.S. PATENT DOCUMENTS

| | | | |
|---|---|---|---|
| 4,886,074 | 12/1989 | Bispine | 607/122 |
| 4,953,564 | 9/1990 | Berthelson . | |
| 5,002,067 | 3/1991 | Borthelsen et al. | 128/642 |
| 5,019,396 | 5/1991 | Ayer . | |
| 5,152,299 | 10/1992 | Soukup | 128/642 |
| 5,239,999 | 8/1993 | Imran . | |
| 5,246,438 | 9/1993 | Langberg . | |
| 5,281,213 | 1/1994 | Milder . | |
| 5,282,844 | 2/1994 | Stokos et al. | 607/121 |
| 5,295,484 | 3/1994 | Marcus . | |
| 5,324,324 | 6/1994 | Vachon et al. | 607/120 |
| 5,342,414 | 8/1994 | Mehra . | |
| 5,411,535 | 5/1995 | Fujii et al. | 607/37 |
| 5,431,649 | 7/1995 | Mulier et al. | 128/642 |
| 5,466,255 | 11/1995 | Franchi | 607/126 |

OTHER PUBLICATIONS

Brugada, Josep et. al. "The Complexity of Mechanisms in Ventricular Tachycardia", Pace, Mar., Part II, pp. 680–686, 1993.

Ferguson, T Bruce; The Future of Arrhythmia Surgery J. Cardiovasc. E. P., vol. 5, pp. 621–634, Jul. 1994.

Nath, S., et al., Basic Aspects of Radiofrequency catheter ablation, J. of Cardiovasc. Electrophysiology, vol. 5, No. 10, 1994, pp. 863–876.

Scheinman, Melvin: Supraventricular Tachycardia: Drug therapy versus catheter ablation, Clinical Cardiology, vol. 17, Suppl. II, 11–15, 1994.

Ganz, L., Friedman, P.: "Supraventricular Tachycardia", NEJM, V332, No. 3, pp. 162–173, Jan. 1995.

Hsia, H. H., et. al.: Work up and management of patients with sustained and nonsustained monomorphic ventricular tachycardias, Cardiology clinics, vol. 11, No. 1, Feb., 1993, pp. 21–37.

Stokes, K., Bornzin, G. The electrode–biointerface: stimulation, in Modern Cardiac Pacing, ed. by. S. Barold, Mount Kisco, NY., Futura, 1985.

*Primary Examiner*—Angela D. Sykes
*Assistant Examiner*—Stephen D. Huang
*Attorney, Agent, or Firm*—Frederick W. Niebuhr, Esq.

[57] ABSTRACT

An implantable devices for the effective elimination of an arrhythmogenic site from the myocardium is presented. By inserting small biocompatible conductors and/or insulators into the heart tissue at the arrhythmogenic site, it is possible to effectively eliminate a portion of the tissue from the electric field and current paths within the heart. The device would act as an alternative to the standard techniques for the removal of tissue from the effective contribution to the hearts electrical action which require the destruction of tissue via energy transfer (RF, microwave, cryogenic, etc.). This device is a significant improvement in the state of the art in that it does not require tissue necrosis.

In one preferred embodiment the device is a non conductive helix that is permanently implanted into the heart wall around the arrhythmogenic site. In variations on the embodiment, the structure is wholly or partially conductive, the structure is used as an implantable substrate for anti arrhythmic, inflammatory, or angiogenic pharmacological agents, and the structure is deliverable by a catheter with a disengaging stylet. In other preferred embodiments that may incorporate the same variations, the device is a straight or curved stake, or a group of such stakes that are inserted simultaneously.

26 Claims, 16 Drawing Sheets

IMPLANTABLE DEVICE FOR THE EFFECTIVE ELIMINATION OF CARDIAC ARRHYTHMOGENIC SITES

BACKGROUND—FIELD OF INVENTION

This invention relates to the field of endocardial mapping, and more particularly to the new field of devices for non-destructive elimination of arrhythmogenic sites and inappropriate conduction pathways, catheter methods for implantation of such devices, and the use of such devices as substrates for local controlled drug release therapy.

BACKGROUND—PRIOR ART

Cardiac arrhythmias are abnormal rhythmic contractions of the myocardial muscle, often introduced by electrical abnormalities, or irregularities in the heart tissue. A region of the heart that results in an arrhythmia is here defined as an arrhythmogenic site in that it introduces the arrhythmia. If a number of regions acting in unison introduce an arrhythmia, they are each considered arrhythmogenic sites. Types of arrhythmogenic sites include, but are not limited to: accessory atrioventricular pathways, ectopic foci, and reentrant circuits.

The anatomical causes of heart arrhythmias are numerous and not entirely understood. Disease and damage to the myocardium from a variety of causes introduce variations in parameters such as conduction and excitability of cells. In turn, such physiological disturbances introduce more complicated spatial and temporal disruption of the electrical synchronization of the heart cells necessary for proper heart function.

Arrhythmias are often classified by where they occur in the heart. Supraventricular arrhythmias occur above the ventricles especially in the atrium or atrio ventricular node. Ventricular arrhythmias occur in the ventricles.

Two of the more common mechanisms of supraventricular arrhythmia generation are accessory pathways and atrioventricular node reentry. Accessory pathways are anomalous bands of conducting tissue that form a connection to the normal atrioventricular conducting system. Typically, in healthy individuals, anatomical regions known as the AV node, His bundle, and bundle branches are the only conduit for the transmission of signals between the atria and the ventricles. Inappropriate accessory pathways are often characterized by rapid conduction and can conduct from atrium to ventricles as well as from ventricle to atrium. These inappropriate conduction pathways result in premature stimuli to some region of the heart by bypassing the normal conduction pathways. Atrio Ventricular reentry tachycardia (AVNRT) has been described as consisting of 2 functionally distinct conduction pathways and has been observed during electrophysiology studies. The two functionally distinct pathways are a fast pathway in which there is rapid signal conduction and a long refractory period, and the second consists of a slow pathway with slow conduction and a short refractory period. In normal or sinus rhythm, the signal is transmitted from the atria to the ventricles via the fast pathway. AVNRT is initiated by atrial premature depolarization where the signal is blocked at the fast pathway because it is still in its longer refractory period. However, the slow conduction pathway has a short refractory period, and is capable of conducting the signal. This can set up a circuit stimulating the fast pathway from the ventricle side, and a reentry circuit within the atrioventricular node is set up. Ten percent of AVNRT cases are believed to be due to a reversal of this situation in which the signal is carried antegrade over the fast pathway and retrograde over the slow pathway. [Ganz, L., Friedman, P.: Supraventricular Tachycardia, New England Journal of Medicine, V. 332, No. 3, pp 162–173, Jan. 19, 1995.]

In general, reentry shall be referred to here as a mechanism whereby the signal propagating through the heart is conducted through a circuit such that it returns to the original site causing premature depolarization of the cardiac cells. Such premature depolarization of surrounding heart cells on a small scale is often sufficient to completely disrupt the action of the heart overall. Reentry can be initiated by fast pathways or by slow pathways caused by a variety of cardiac diseases and is believed to be the cause of many arrhythmias. Reentry can also happen in any region of the heart.

For example, in a myocardial infarction, or heart attack, cells die due to lack of nutrients because the blood vessel that provides the nutrients is obstructed. As the site of infarction heals, the dead myocardium is replaced by fibrous tissue and the residual viable myocardial cells become embedded in scar leading to non-uniform activation and slow conduction. These abnormalities provide a substrate for reentry which may initiate a ventricular arrhythmia.. [Hsia, H.H. et. al., "Work -Up and Management of Patients with Sustained and Non sustained Monomorphic Ventricular Tachycardias", Cardiology Clinics, Vol. 11, No. 1, pp 21–37, February, 1993].

A schematic of one such reentry circuit is shown in FIG. 1. Because the surviving tissue 32 in the center of the necrotic tissue 30a and 30b has higher resistance to the incoming electrical signal 34, the signal 36 travels around the necrotic region 30b, and excites the embedded surviving tissue 32 on the far side of the necrotic region. The excitation of surviving tissue 30 often results in stimulation of cells that have already fired when reentry of the signal 38 occurs. In turn, surrounding cells 28 are then affected.

Arrhythmias can result from the propagation of an impulse around a large necrotic scar in what can be called a macro reentrant circuit. In this type of circuit, the impulse propagates as a broad wave front around the obstacle. If the obstacle is sufficiently large, there is no need for a well defined area of slow conduction. Arrhythmias can also be due to a reentrant circuit where the impulse propagates around a fixed obstacle in which a well defined area of myocardium is a necessary path in the circuit. Other mechanisms are also possible. [Brugada, Josep, et. al., "The Complexity of Mechanisms in Ventricular Tachycardia", Pace, March, Part II, pp 680–686, 1993]. A simple schematic of a reentry circuit introduced by a fixed obstacle is shown in FIG. 2. Here the necrotic tissue or region of slow conduction 30 results in a reentry signal 38 which disrupts the function of the surrounding myocardial cells 28.

Necrotic regions that act as arrhythmogenic sites may depend upon other arrhythmogenic sites to introduce an arrhythmia, just as the presence of other arrhythmogenic sites may complicate an arrhythmia. In FIG. 3, a figure of eight functional circuit is shown. This circuit consists of two reentrant regions 38a and 38b that are essentially coupled. Here, a slightly more complicated reentrant circuit is shown to be introduced by two separate regions of dead tissue 30c and 30d. Although they act together, each of these regions is an arrhythmogenic site.

Surgical techniques exist to treat arrhythmias, and the selection of the most appropriate technique often depends upon the type of arrhythmia that is believed to be present. Most of these involve destroying the electrical action of the tissue to block one or more inappropriate conduction pathways. Interruption of a presumed reentrant circuit or complete isolation of the problem region have been attempted by a variety of techniques.

A surgical technique, called the Maze procedure, has been used for treating Supra Ventricular Tachycardias. In the Maze procedure, a number of incisions are made in an attempt to terminate inappropriate accessory pathways. [Furguson, T. Bruce; The Future of Arrhythmia Surgery, J. Cardiovascular E.P., Vol. 5, pp 621–634, Jul. 1994.] This technique is hazardous for the patient in that it requires open heart surgery. The procedure is complex in that it required a number of precisely located delicately introduced incisions in the heart wall. The procedure is innovative in that it may result in a cure, but it is expensive and risky for the patient due to its complexity.

A new series of procedures and techniques for interrupting a current pathway in the heart or isolating tissue exist. In these procedures, the arrhythmogenic region is isolated or the inappropriate pathway is disrupted by destroying the cells in the regions of interest. Using catheter techniques to gain venous and arterial access to the chambers of the heart, necrotic regions can be generated by destroying the tissue locally. These necrotic regions effectively introduce electrical barriers to problematic conduction pathways. The destruction of tissue is called ablation, and there are various ablation catheters and techniques for their use. The ablation mechanism is typically energy transfer such as the delivery of heat, ultrasound, radio frequency energy, microwave energy, laser energy, or the removal of energy via cryogenic cooling. The most popular of these uses RF energy such as discussed in U.S. Pat. No. 5,246,438.

The theoretical effect of ablation on the reentry mechanisms shown is shown in FIGS. 4, 5, and 6, in which the circuits of FIGS. 1, 2, and 3 are treated with an ablative procedure. In FIG. 4, the interruption 40 to the circuit is introduced by destructively introducing a non conductive region 42 of necrotic tissue to interrupt the circuit. In FIG. 5, the interruption 40 to the anatomical circuit is introduced by destructively introducing a non conductive region 42 of necrotic tissue to interrupt the circuit. In FIG. 6, the interruption to the two circuits 40a and 40b is introduced by destructively introducing a single non conductive region 42 of necrotic tissue to interrupt the circuit. In FIGS. 4, 5, and 6, the ablative procedure is shown to interrupt the reentrant pathway successfully.

Ablation procedures for tissue isolation or interruption are based upon the destruction of tissue in the vicinity of the arrhythmogenic site. Typically a standard procedure involves a number of attempted ablations before a procedure is successful. A typical procedure involves the destruction of much more tissue than that required to terminate the arrhythmia, and much of this is unnecessary damage. There is a need for a new and improved technique of eliminating arrhythmogenic sites without causing unnecessary damage to the tissue.

In addition, the ablation techniques in use today such as those described in U.S. Pat. Nos. 5,295,484 and 5,246,438 are irreversible. Typically the electrophysiologist will ablate a region to eliminate an arrhythmogenic site, perform an evaluative test, and introduce more tissue damage by ablation until the arrhythmia is cured or until the electrophysiologist determines that the procedure will be unsuccessful. Since the dead tissue cannot be restored after each evaluation, the procedure is irreversible. If the tissue could be wholly or partially restored, there would be less dead tissue, and fewer problems introduced by the dead tissue.

Evaluation of the effect prior to the destruction of tissue would result in less dead tissue for a successful procedure. The techniques involving cooling of the tissue, such as described in U.S. Pat. No. 5,281,213 do allow a physician to temporarily inactivate the tissue by cooling it to a temperature which does not cause tissue necrosis, but that region of tissue is quickly returned to its normal state by the heat of the surrounding tissue. This temporary treatment is too short to allow for any but the most cursory evaluation of results. In addition, if the temporary cooling is deemed successful, the procedure must be repeated allowing the introduction of procedural errors. There is a need for a technology that will allow an Electrophysiologist the option to attempt to eliminate the arrhythmogenic site reversibly. Reversibility would allow evaluative tests to be performed, and the procedure to be modified based upon the results of the test or tests performed, without unnecessary destruction of tissue.

In addition, existing ablation techniques which involve complicated energy transfer mechanisms require approximations on the amount of myocardial tissue necrosis resulting from the destructive energy transfer mechanism used. Repeatability and reliability of a procedure that varies inherently is extremely difficult. Attention is currently being focused on establishing parameters and techniques such that the geometry of the ablated region of myocardium can be more precisely controlled. Such mechanisms are also often limited in that they cannot eliminate tissue at a specified depth within the myocardium, but rather must typically begin destruction at the surface of the endocardium and move inwards until the desired depth is achieved. There is a need for a technique that will allow more precise electrical removal of arrhythmogenic sites in the myocardium.

One of the primary limitations of ablation techniques is the inability of the thermal action of RF energy to penetrate to arrhythmogenic sites deep in the heart wall. The inability to penetrate with the thermal action of RF energy is the driving force behind development of microwave and ultrasound ablation systems [Nath, S., DiMarco, J. P., Haines, D.: Basic Aspects of Radiofrequency Catheter Ablation, J. of Cardiovascular Electrophysiology, Vol. 5, Nov. 10, 1994 pp 863–876]. There is a need for a means of eliminating arrhythmias at a depth within the heart tissue.

Existing ablation techniques have a further drawback in that they may generate bubbles or introduce thrombosis formation in the heart. Bubbles and thrombosis are not considered problematic in the right heart because they will be trapped in the region of the lungs. However, bubbles or thrombosis could very easily be fatal or introduce brain damage if introduced in the left heart chambers. There is a need for a means of eliminating arrhythmogenic sites that does not introduce bubbles or thrombosis into the heart chamber such that the same technique may be used in the left and the right heart chambers.

The variety of ablation techniques for the treatment of cardiac arrhythmias are independent procedures that are coupled with pharmocologic therapy. Physicians must typically decide whether to pursue drug therapy, ablation, both, or neither depending upon a particular patients requirements. Just as there are a number of ablation techniques for the treatment of arrhythmias, there are a number of viable pharmocologic therapies that are also available. Drugs that predominantly affect slow pathway conduction include digitalis, calcium channel blockers, and beta blockers. Drugs that predominantly prolong refractoriness or time before a heart cell can be activated, produce conduction block in either the fast pathway or in accessory AV connections including the class IA antiarrhythmic agents (quinidine, procainimide, and disopyrimide) or class IC drugs (flecainide and propefenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Melvin: Supraventricular Tachycardia: Drug Therapy Versus Catheter Ablation, Clinical Cardiology Vol 17, Suppl. II-11–II-15 (1994)].

These and other drugs that may be used in the treatment of cardiac disease are typically introduced orally or intravenously and would be more viable if they could be delivered directly into the myocardium at the region of interest using controlled drug release technology. Controlled drug release is an existing and developing technology for the local delivery of a drug over an extended period of time. The mechanisms typically used for controlled drug release are diffusion control systems, biodegradable systems, osmotic systems, and mechanical systems. Controlled drug release provides a number of advantages. Among them are: more constant agent levels over time, site of action delivery of the agent, reduced dosage and side effects, and less frequent administration.

A delivery dispenser for treating cardiac arrhythmias is disclosed in U.S. Pat. No. 5,019,396 by Ayer et. al. In this patent, an innovative construction for an osmotic delivery of drugs for treating arrhythmias is disclosed. Ayer et. al. does not discuss treatment locations other than via the gastrointestinal tract which is accessed orally. They do not provide for local delivery of the drug to the heart, but only for controlled release into the gastro intestinal tract. To obtain the full benefits of controlled drug release technology for the treatment of arrhythmias, a method and means to deliver controlled drug release therapy directly to an arrhythmogenic site are needed.

No prior art has been located in which controlled drug release has been attempted frown within the heart to treat arrhythmias, and more specifically at the site of a suspected arrhythmogenic site. However, some preliminary work has been performed using controlled release matrices located epicardially in an animal model.

Controlled release matrices are drug polymer composites in which a pharmacological agent is dispersed throughout a pharmacological inert polymer substrate. Sustained drug release takes place via particle dissolution and slowed diffusion through the pores of the base polymer. Prior work has shown that antiarrhythmic therapy administered by epicardial application of controlled release polymer matrices is effective in treating and preventing ventricular arrhythmias in canine ventricular tachycardia model systems [Siden, Piuka, et. al.: Epicardial Controlled Release Verapimil Prevents Ventricular Tachycardia Episodes Induced by Acute Ischemia in a Canine Model, J. Cardiovascular Pharmacology 19:798-809, Nov. 5, 1992.] This work shows the viability of controlled release therapy delivered locally for the treatment of arrhythmias, but no means of introducing the agents directly to the arrhythmmogenic site has been developed. There is a need for a means of delivering a controlled release matrix or other such structure into the heart such that controlled drug release therapy may be pursued at specific regions within the heart for cardiac arrhythmias and other disorders.

U.S. Pat. No. 4,953,564 combines a cardiac stimulation lead and a drug incorporated into a controlled release device, such that the drug delivery is directed to the region to be stimulated with electrical energy. The focus of U.S. Pat. No. 4,953,564 is on controlled release of antiinflamitory agents to the tissue, and it does not discuss anti arrhythmic agents, growth factors, local delivery to angiogenic sites, or endocardial drug delivery without the lead in place. Steroids have been used effectively in pacing leads to limit tissue response to the implanted lead, and to maintain the viability of the cells in the region immediately surrounding the implanted device. Angiogenic factors are derived growth factors which result in the proliferation of new capillary growth, and anti-inflammatory agents are here defined as agents for the reduction of tissue response to the implanted device. There is a need for a means for endocardial controlled drug release therapy at specific sites using antiarrhythmic agents, growth factors, and anti inflammatory agents.

OBJECTS AND ADVANTAGES

In general it is an object of the present invention to provide an implantable biocompatible device, and means for implantation of the device in the region of an arrhythmogenic site to effectively eliminate arrhythmogenic sites from the myocardium.

Another object of the invention is to provide a system and method of the above character that introduces little damage upon implantation such that it is essentially reversible. A reversible procedure allows an electrophysiologist the option to effectively interrupt, isolate, or otherwise effectively electrically remove or reduce the arrhythmogenic effects of a region of the myocardium that is believed to be the arrhythmogenic site, to perform evaluative tests if desired, and to modify the procedure only if desired based upon the results of the test or tests performed.

Another object of the invention is to provide a system and method of the above character in which the electrical disruptions introduced by the device into the myocardium are accurate and repeatable such that the effects on the arrhythmogenic sites in the myocardium may be introduced accurately and repeatably.

Another object of the invention is to provide a system and method of the above character in which the effects introduced into the myocardium may be altered by selecting different conductive and non conductive materials.

Another object of the invention is to provide a system and method of the above character in which the electrical disruptions introduced by the device into the myocardium are accurate and repeatable such that the effects on the arrhythmogenic sites in the myocardium may be introduced accurately and repeatably.

Another object of the invention is to provide a system and method of the above character in which the effects introduced into the myocardium may eliminate arrhythmias at any depth within the heart tissue.

Another object of the invention is to provide a system and method of the above character that allows for treatment of arrhythmogenic sites in the left heart in that no bubble formation resulting from energy delivery, and no thrombosis will be formed.

Another object of the invention is to provide a system and method of the above character in which the permanently implantable device acts as a substrate for delivering pharmacological anti arrhythmic agents, anti thrombogenic agents, angiogenic factors, and/or steroidal anti inflammatory agents over an extended period of time directly to endocardial regions, such as arrhythmogenic sites Another object of the invention is to provide a method and means to deliver controlled drag release therapy directly to endocardial regions, such as arrhythmogenic sites.

Further objects and advantages of my invention will become apparent from a consideration of the drawings and ensuing description.

Figure 1:
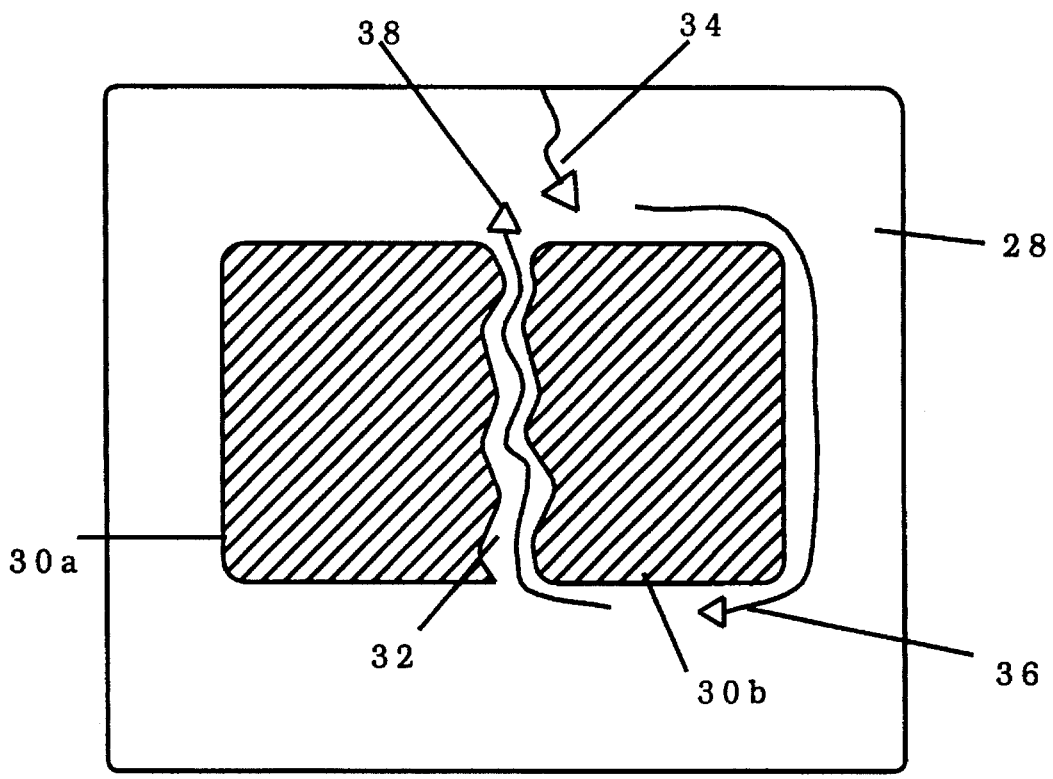
FIG. 1 is a schematic of an anatomical circuit with a surviving bundle of tissue across the necrotic region.
Figure 2:
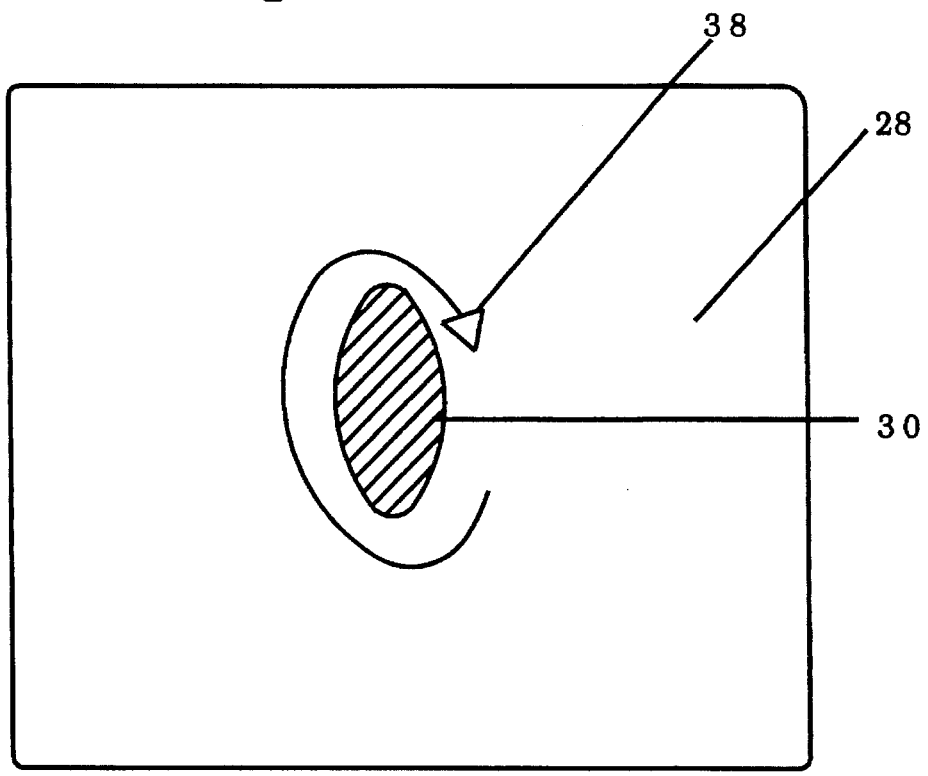
FIG. 2 is a schematic of an anatomical circuit around a necrotic area.
Figure 3:
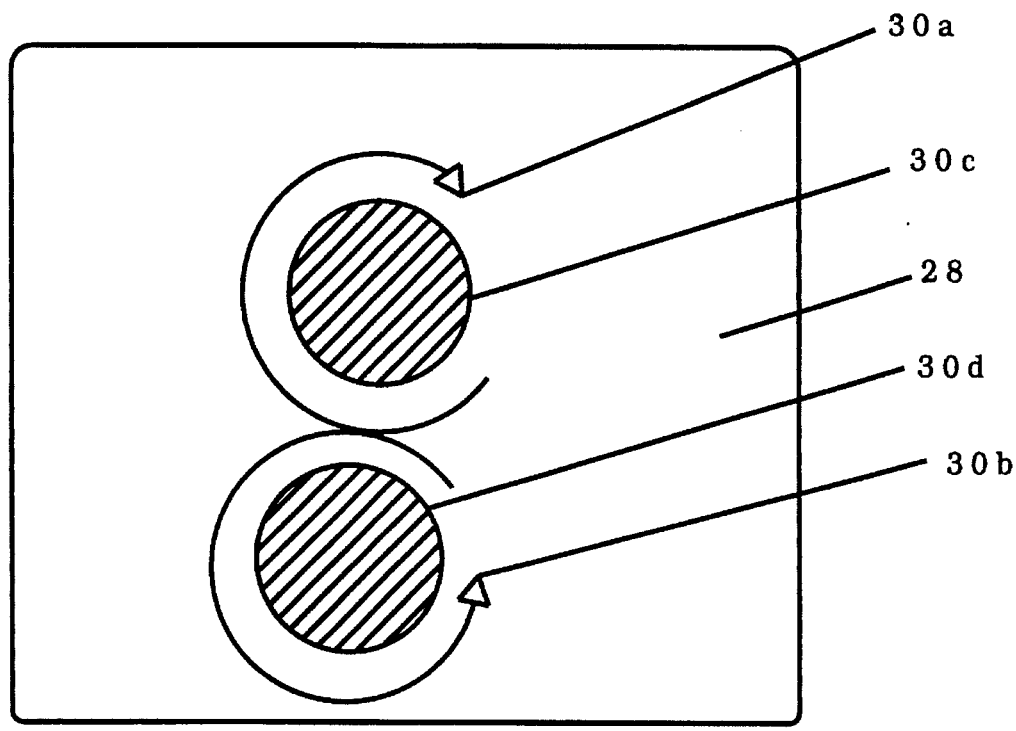
FIG. 3 is a schematic of a figure of eight functional circuit.

List of Reference Numerals:

| | |
|---|---|
| 28 | Normal Heart Tissue |
| 30 | necrotic tissue |
| 30a | necrotic tissue |
| 30b | necrotic tissue |
| 30c | necrotic tissue |
| 30d | necrotic tissue |
| 32 | surviving tissue |
| 34 | incoming electrical signals |
| 36 | signal |
| 38 | reentry |
| 38a | reentry |

-continued

List of Reference Numerals:

| | |
|---|---|
| 38b | reentry |
| 40 | interruption to the circuit |
| 42 | nonconductive region generated by ablation |
| 44 | tip |
| 46 | helix |
| 47 | length of helix |
| 48 | diameter |
| 50 | spacing |
| 52 | structure diameter |
| 53 | structure |
| 54 | head |
| 56 | distance |
| 58 | rigid core |
| 60 | matrix |
| 62 | circular opening |
| 64 | elliptical region |
| 66 | protective catheter jacket |
| 68 | outer stylet |
| 70 | outer stylet lumen |
| 72 | inner stylet |
| 74 | recessed balls |
| 76 | circular opening in outer stylet |
| 77 | Catheter electrode for mapping |
| 78 | knob |
| 79 | Electrode for mapping through helix |
| 80 | inner stylet proximal end |
| 81 | Catheter electrode for mapping |
| 82 | positioning disk |
| 83 | proximal electrical connections |
| 84 | rigid metallic structure |
| 84a | exposed rigid metallic structure |
| 85 | conductor |
| 86 | central loop |
| 87 | conductor |
| 88 | clockwise female threads |
| 89 | conductor |
| 90 | counter clockwise female threads |
| 91 | ramp for inner stylet |
| 92 | stake |
| 94 | distal end |
| 96 | barb |
| 98 | head on proximal end of stake |
| 99 | arrhythmogenic site |
| 99a | arrhythmogenic site |
| 99b | arrhythmogenic site |
| 100 | cage |
| 102a | stake |
| 102b | stake |
| 102c | stake |
| 102d | stake |
| 104 | center |
| 106 | sharp ends |
| 108 | barb |
| 110 | head on cage |
| 112 | Opening on cage |
| 114 | jacket |
| 115 | lumen |
| 116 | release |
| 118 | pivot |
| 120 | catheter catch |
| 122 | stylet catch |
| 124 | spring |
| 126 | stylet |
| 128 | male threads on stylet |
| 130 | female threads on stylet catch |
| 132 | two filar coil |
| 134 | connection to coil |
| 136 | crimp |

-continued

List of Reference Numerals:

| | |
|---|---|
| 138a | mapping electrode |
| 138b | mapping electrode |
| 139a | connection to mapping electrode |
| 139b | connection to mapping electrode |
| 140 | connection to coil |
| 141 | positioning disc |
| 142 | crimp |
| 143a | embedded conductor |
| 143b | embedded conductor |
| 144 | cage recess |
| 146 | stake |
| 1488 | incoming signal |
| 150 | conductive helix |
| 152 | outcoming signal |
| 152a | outcoming signal |
| 152b | outcoming signal |
| 152c | outcoming signal |
| 152d | outcoming signal |
| 154 | insulative helix |
| 156 | small drug embedded polymer |
| 158 | large drug embedded polymer |
| 160 | drug embedded polymer surface |
| 162 | lumen of drug delivery catheter |
| 164 | hollow helix |
| 166 | apertures in hollow helix |
| 168 | head of hollow helix |
| 184 | heart septum |
| 186 | heart |
| 188 | right ventricle |
| 190 | drug delivery catheter |
| 192 | hollow helix with drug delivery |

SUMMARY

An implantable device for the effective elimination of an arrhythmogenic site from the myocardium is presented. By inserting small biocompatible conductors, insulators, and/or combinations thereof into the heart tissue at the arrhythmogenic site, it is possible to effectively eliminate the arrhythmogenic effects of a portion of the tissue from the electric field and current paths within the heart. In addition, the structure and delivery techniques allow for endocardial controlled drug release therapy to any region of tissue selected.

DETAILED DESCRIPTION OF PREFERRED EMBODIMENTS

Figure 7:
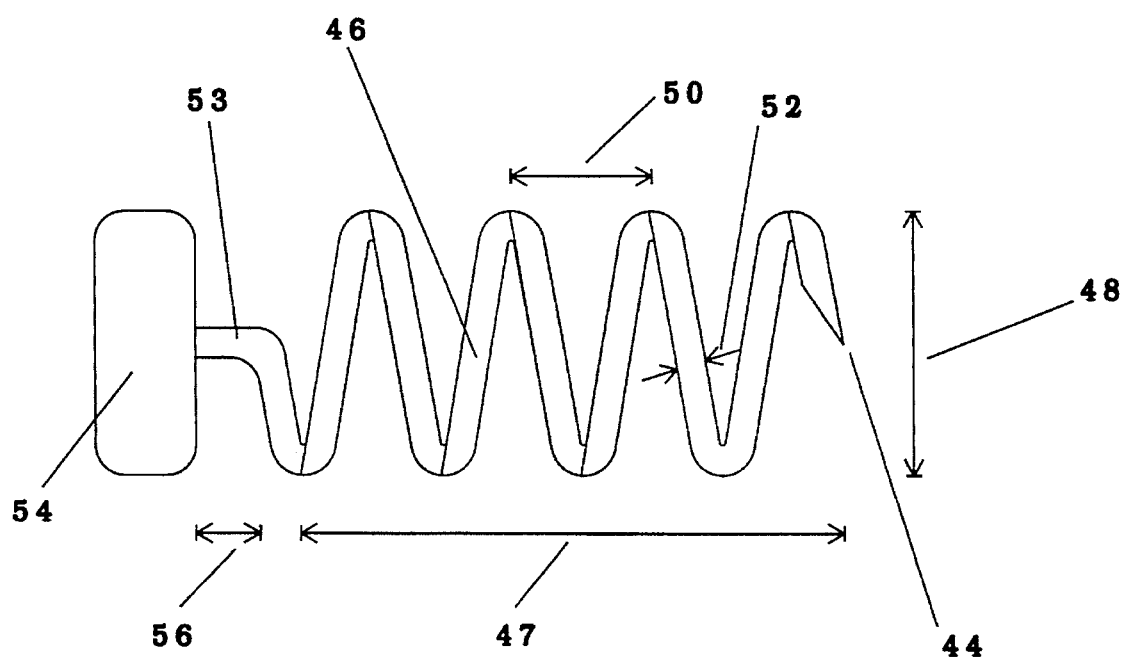
FIG. 7 is a perspective view of a helix embodiment of this invention.

FIG. 7 shows a perspective view of a helix embodiment of this implantable device. In this preferred embodiment, the entire structure is made of a biocompatible Platinum Iridium alloy that can be formed using investment casting, machining or other similar techniques. The helix embodiment shown has a sharp tip 44 to allow for ease in advancing the helical structure into the heart wall. A number of loops of a helix 46 have the same diameter 48 and spacing 50 to prevent excessive damage to the myocardium upon insertion. By having the same diameter 48 at each cross section of the helix 46 and spacing 50 between the loops of the helix 46 the path through the myocardium followed by each loop of the helix 46 will be the same. The spacing 50 can vary from very tight spacing in which distance 50 between the two loops of helix 46 are approximately two times the size of diameter 52 of structure 53 that defines helix 46 to loose spacing in which distance 50 between the two loops of helix 46 are approximately twenty times diameter 52 of the structure 53 formed into a helix. The diameter 52 of structure 53 of helix 46 is not necessarily constant throughout the length of helix 46. The diameter 52 of looping structure 53 can vary such that it is larger at any given portion of helix 46. Having the structure larger near a proximal end, connection site, or head 54 would facilitate insertion, and having it larger in the vicinity of the arrhythmogenic site may facilitate isolation of the arrhythmogenic site. Although the cross section of the structure 53 of the helix 46 could vary in both size and shape and not affect the functionality, the cross section of the preferred embodiment is circular and uniform to minimize the damage to the tissue upon insertion. Head 54 is connected on one end to provide connection means for introducing the device into the heart and for advancing the device into the heart wall. Distance 56 from head 54 to the beginning of helix 46 should be small to prevent excessive protrusion of the head from the heart wall. Helix diameter 48 should be no larger than one and a half centimeters, and no smaller than one millimeter in diameter. The maximum overall length 47 of the helical portion of the device would be equal to the thickest wall region of the human heart.

Figure 8:
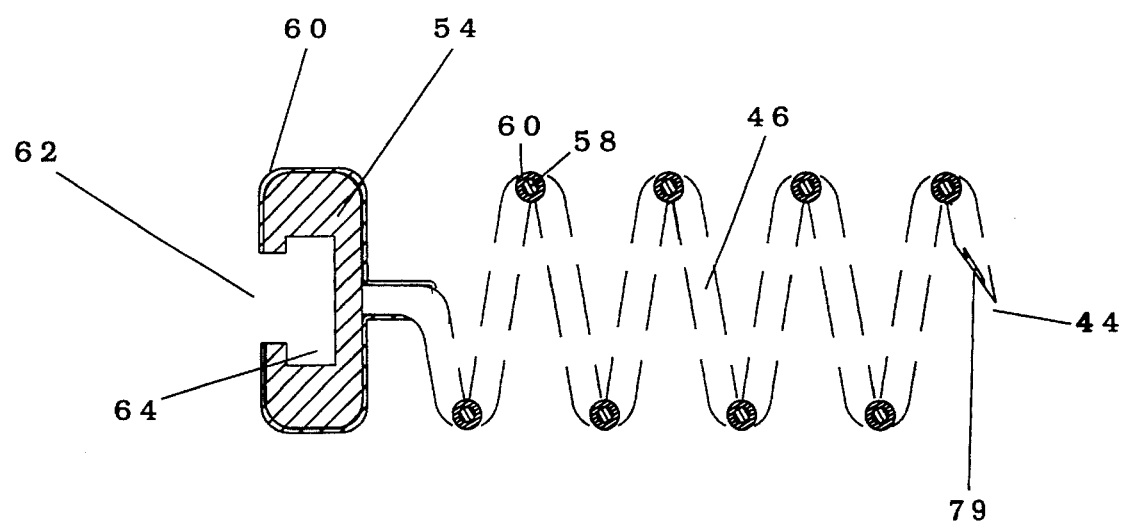
FIG. 8 is a section view of a helix embodiment.

FIG. 8 shows a cross section view of another preferred helix embodiment of this implantable device. Here, helix 46 is constructed with a rigid core material 58 coated or covered with an insulative controlled release matrix 60. Matrix 60 is a drug diffusion polymer system for the sustained release of drugs such as is disclosed in U.S. Pat. No. 5,342,628. In other preferred embodiments, matrix 60 uses biodegradable polymer drug systems or other state of the art controlled drug release systems to achieve controlled drug release from the device. Matrix 60 covers head 54 except in the region where the delivery catheter connects to head 54. Head 54 has a circular opening 62 that becomes elliptical deeper into the head. The elliptical region 64 provides a means for effective connection of the delivery catheter to the implantable device. Tip 44 of the helix embodiment will consist of exposed conductive metals, such as Platinum Iridium, as shown by exposed region 79 for applications where tip 44 of helix 46 acts as a sensing electrode.

Figure 9:
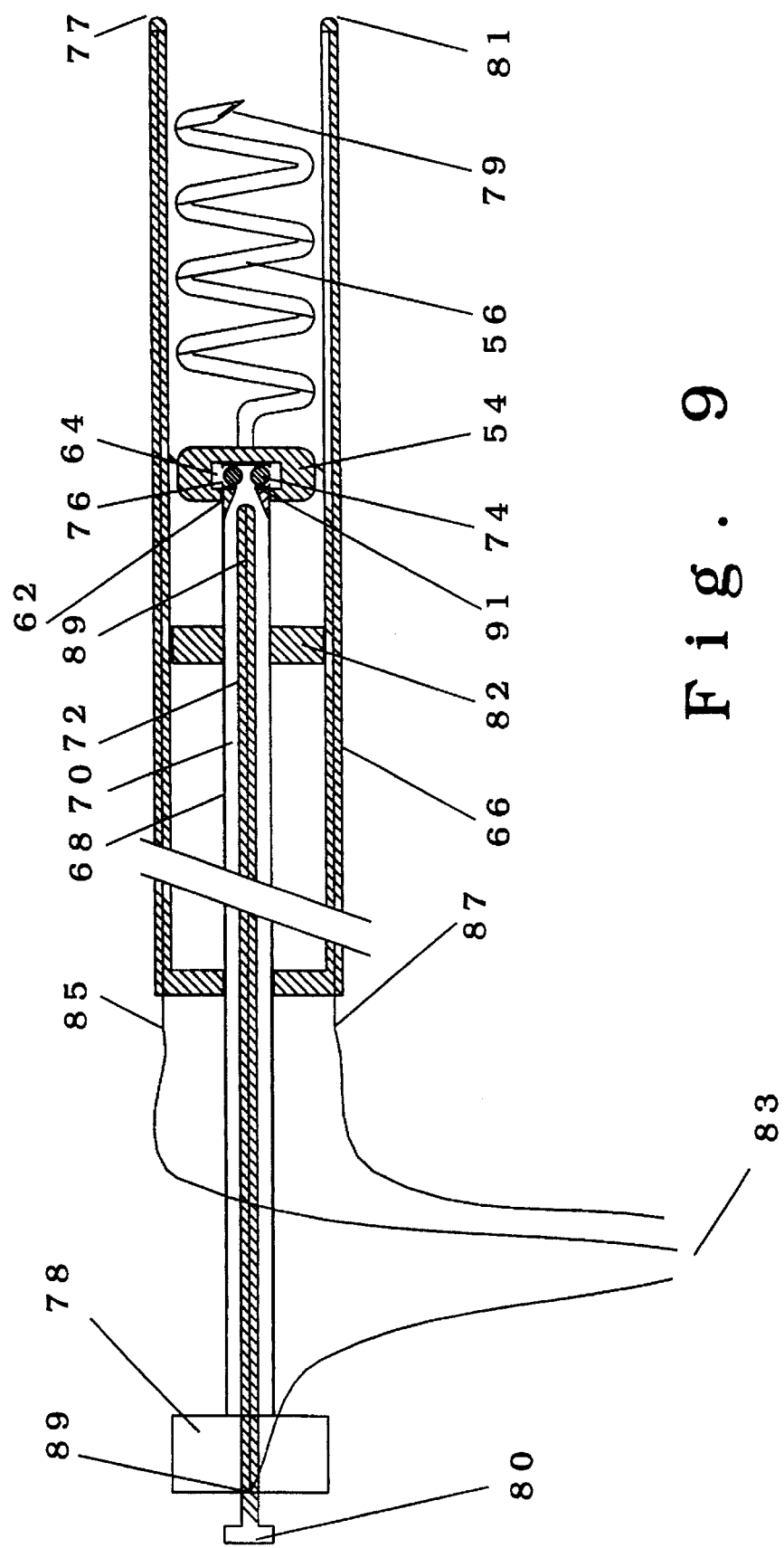
FIG. 9 is a section view of a catheter delivery system for a helix embodiment.

FIG. 9 shows a cross sectional view of a preferred embodiment of a delivery catheter for implantation of the helix embodiment of the implantable device. Helix 46 is housed in a protective catheter jacket 66 that prevents the helix 46 from catching on tissue during venous or arterial access to the heart chamber in which it is to be implanted. Jacket 66 can be made from a number of standard materials used in standard cardiac catheter construction such as, but not limited to, polyurethane and flouropolymers. An advancable outer stylet 68 has a diameter smaller than the circular opening 62 on head 54 such that outer stylet 68 may be advanced inside circular opening 62 on head 54. Outer stylet 68 is not a solid structure, but has an inner lumen 70 in which an inner stylet 72 can be advanced to engage outer stylet 68 with head 54 with recessed balls 74 in the distal region of outer stylet 68. Advancing inner stylet 72 results in protrusion of balls 74 from circular openings 76 smaller in diameter than balls 74. The recessed balls 74 will provide a means of delivering torque for introducing the helix device into the heart wall. Since inner elliptical chamber 64 will not allow outer stylet 68 to rotate in head 54 with balls 74 protruding from circular opening 76 torque may be delivered from knob 78 connected to proximal end of outer stylet 68 to helix 46. Disengagement of helix from catheter introduces no forces on the heart. Inner stylet 72 is retracted at proximal end 80 such that balls 74 no longer protrude from outer stylet 68, which may then be removed from head 54. Balls 74, inner stylet 72 and outer stylet 68 may be made from medical grade stainless steels, titanium or the equivalent. Near the distal end of outer stylet 68 is a positioning disc 82 which slides easily in jacket 66. Positioning disc 82 maintains the position of outer stylet 68 on the central axis of jacket 66 for quick engagement or disengagement of outer stylet 68 with head 54. Inner stylet 72 may be curved to introduce curvature to the delivery catheter as a whole to improve ease of accessing certain regions of the heart. A curved inner stylet would be guided by external stylet 68 into its appropriate position between balls 74. Ramp 91 for inner stylet 72 allows for precise positioning of inner stylet 72 between balls 74 at the distal end of external stylet 68. Ramp 91 acts as a collar guiding internal stylet 72 into the center of external stylet 68. In another preferred embodiment, external stylet 68 could be very short on the end of a coiled guidwire such that inner stylet 72 slides down the center of the very flexible coil guidwire imparting its shape more effectively to the catheter as a whole. Two distal electrodes 77 and 81 for mapping the electrical action on the endocardium are positioned 180 degrees apart. These electrodes provide means for performing electrophysiology measurements before during and after implantation of the device. In other embodiments additional electrodes could be positioned along the body of the catheter such that the delivery catheter doubles as a standard multipolar electrophysiology mapping catheter. The conductors 85 and 87 that connect to distal mapping electrodes 77 and 81 may be extruded into the outer jacket 66 for proximal connection 83. In addition, tip 79 of helix 46 is an exposed conductive substrate of helix 46 such that mapping of electrical action at the tip during the implantation of helix 46 is possible. The electrical signal on the endocardium is be transferred through the helix substrate 58 to the internal stylet 72 through conductor 89 to the proximal connections 83.

Figure 10:
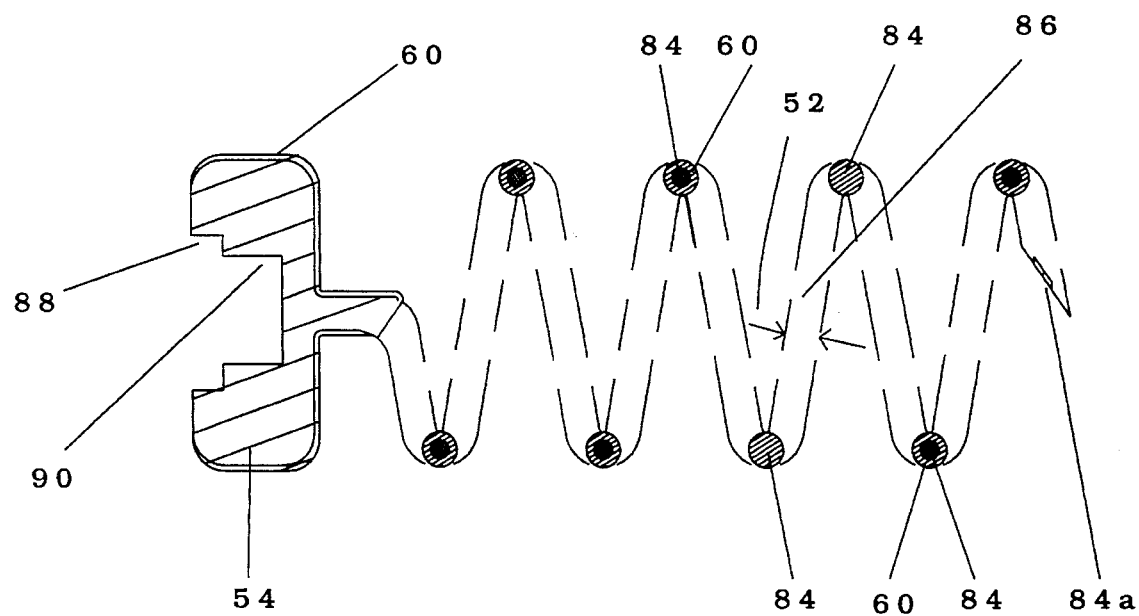
FIG. 10 is a sectional view of a helix head with concentric threads.

FIG. 10 shows a cross sectional view of another preferred embodiment of this implantable device. Drug release matrix 60 does not cover the central loop 86 of helix 46 resulting in exposure of a rigid metallic structure 84. In the preferred embodiment, the rigid metallic structure 84 that is exposed in central loop 86 has the same diameter 52 as the regions of the helix 46 covered with matrix 60. Investment casting of the rigid metallic structure 84 in a platinum iridium alloy such that the diameter 52 is larger in the central loop 86 of helix 46 and coating the device with matrix 60 such that the exposed rigid metallic region defines the outer diameter is one possible fabrication means. Although the embodiment shown has only one loop of exposed metal, other embodiments ranging from exposed metal on a number of loops to exposure on a portion of a loop are possible. Head 54 depicts another embodiment of the catheter engagement mechanism for implantation of the helix device. Here, clockwise female threads 88 are concentrically located in head 54 around a second smaller set of counter clockwise female threads 90 located on the axis of the helix 46. Together, threads 88 and 90 allow transmission of torque in both the clockwise and counterclockwise directions. Bi-directional transmission of torque allows the device to be inserted and withdrawn from the myocardium. Torque is delivered in the appropriate direction with two different sized stylets. One stylet would be larger and thread into external threads 88 for insertion into the myocardium. A second stylet would be of a smaller diameter such that it is not affected by the external threads 88, and thread into internal threads 90 deeper in head 54 of the device. Internal threads 90 are used for removal of a helix embodiment from the myocardium.

Figure 11:
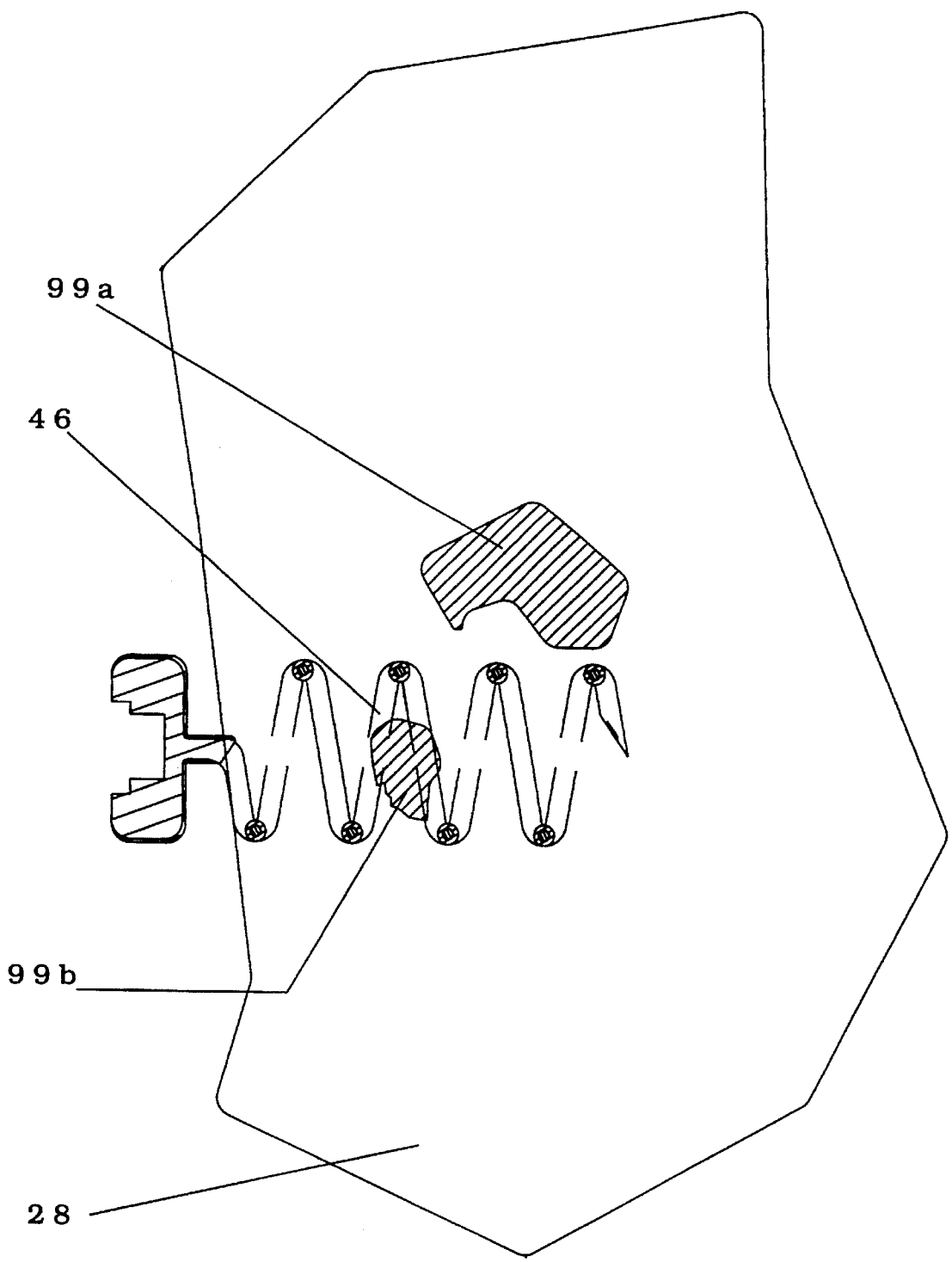
FIG. 11 is a cross sectional view of a helix embodiment implanted in the heart wall.

FIG. 11 shows a sectional view of a variation of the helix embodiment shown in FIG. 10 embedded in the heart wall 28. Here, there is no conductive region such as central exposed loop 86 in FIG. 10. Instead the entire surface is insulative. Positioning of insulated helix 46 is adjacent to arrhythmogenic site 99a and around arrhythmogenic site 99b. In this way, the conduction pathways and potential gradients in the region of the arrhythmogenic site can be modified to eliminate or reduce the disruptive effects of the local myocardium. It is necessary that the helix be made of a material or combination of materials such that the complete structure is rigid enough to be screwed into the heart wall. Arrhythmogenic sites 99a and 99b if separate from the other could be treated with the implantation of helix 46, just as they may be treated together. Just as a plurality of devices may be used to treat a single arrhythmogenic sites, a single device may be used to treat a plurality of arrhythmogenic sites.

Figure 12:
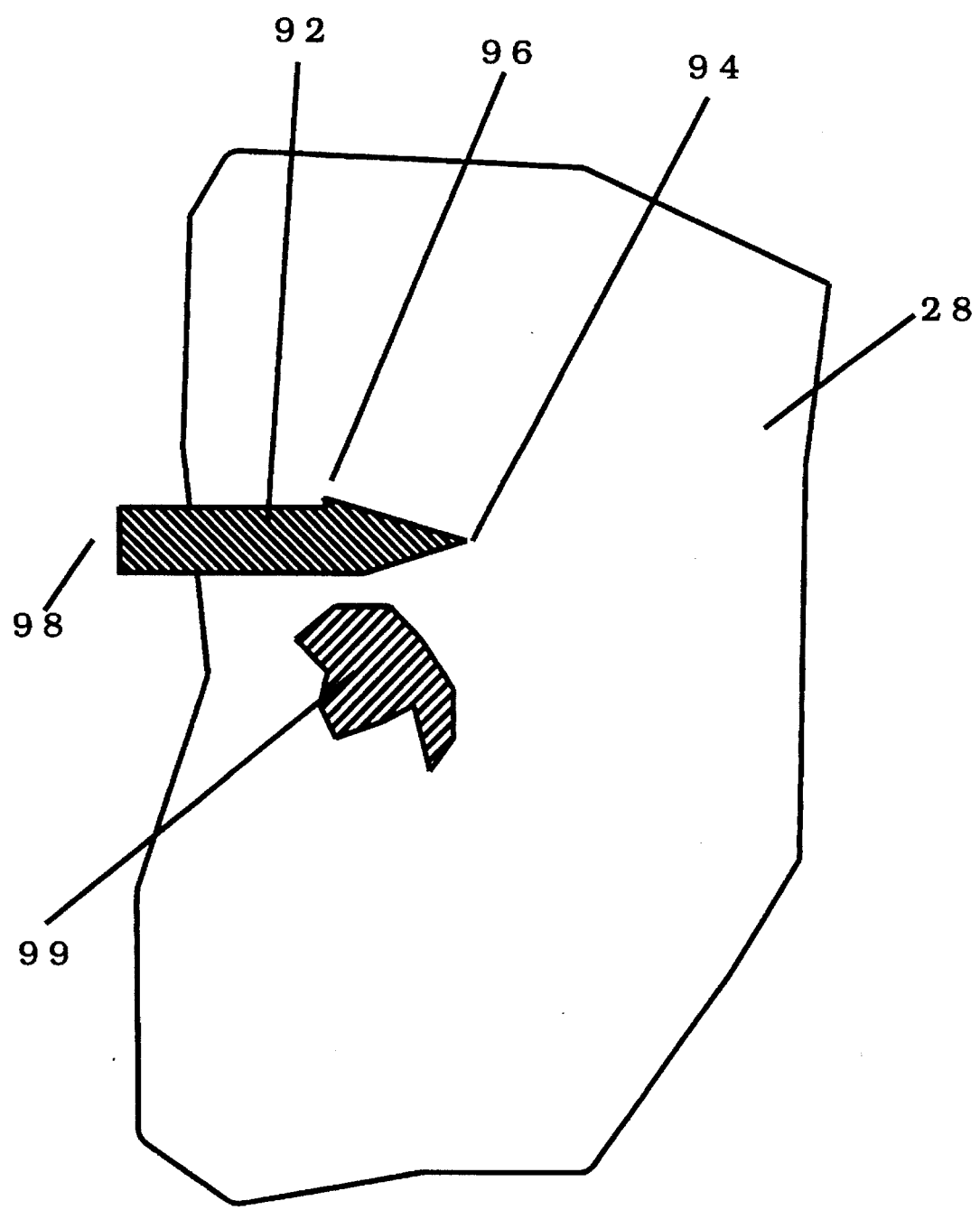
FIG. 12 is a sectional view of a stake embodiment implanted in the heart wall.

FIG. 12 shows a cross sectional view of another preferred embodiment in which the geometry of the structure that is inserted into heart wall 28 is a stake 92. The cross section of stake 92 perpendicular to the axis of insertion is circular in the preferred embodiment, but it could also be elliptical, rectangular, or triangular. In the preferred embodiment stake 92 is straight such that the implanting physician will know the direction the stake will go under standard fluoroscopy. A curved stake may require biplanar fluoroscopy to confirm the direction that the stake would travel upon penetration of the heart muscle. Stake 92 is sharp at its distal most end 94 to facilitate insertion into the heart wall 28. A single stake 92 may be sufficient to disrupt an arrhythmogenic site, or it may be used to augment the effectiveness of additional stakes 92 and other devices such as the helix embodiment shown in FIG. 8. Stake 92 is implanted adjacent to arrhythmogenic site 99. A head 98 on the proximal end of stake 92 should be broad and flat to provide a surface for applying force for insertion of the stake into heart wall 28. In this embodiment, stake 92 has a small barb 96 on its distal end to prevent migration or dislodgment after implantation.

A number of stakes may be inserted with one or more catheter delivery systems to surround an arrhythmogenic site if necessary. A number of stakes could be lined up within the lumen of the delivery catheter such that they are advanced one at a time into their different positions within the heart wall. A controlled advancement of each stake could be performed with a simple stylet that would advance a controlled amount for each stake's insertion.

Figure 13:
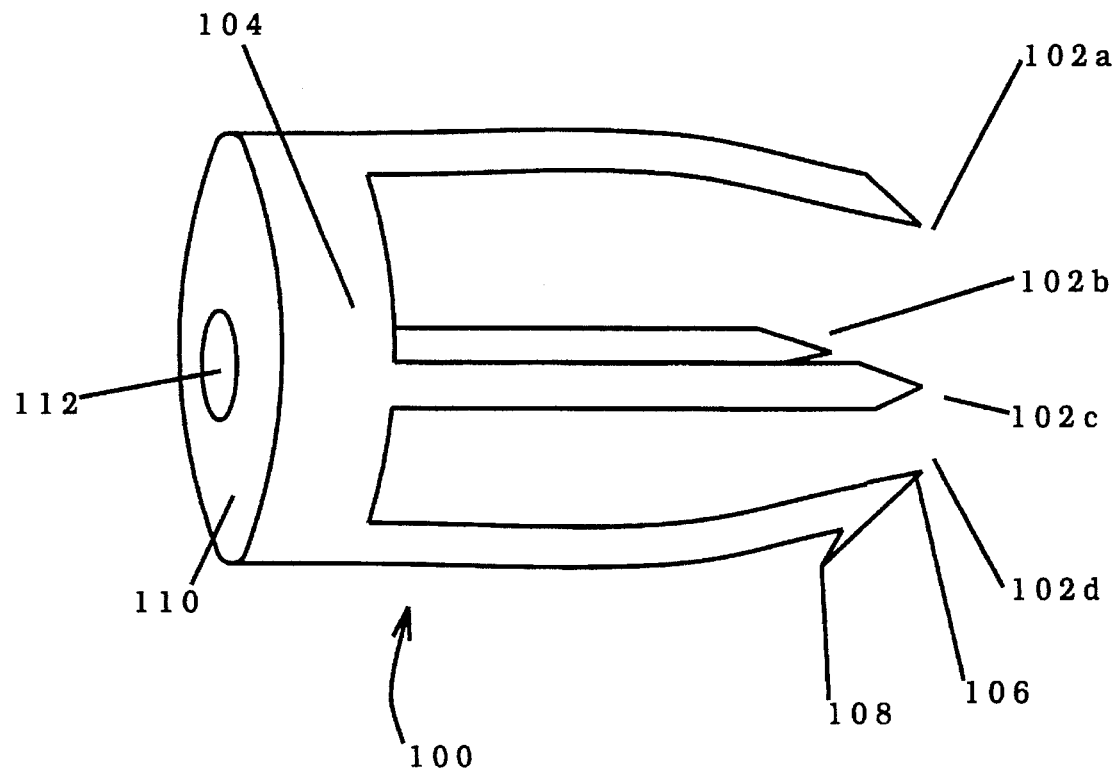
FIG. 13 is a perspective view of a cage embodiment.
Figure 22:
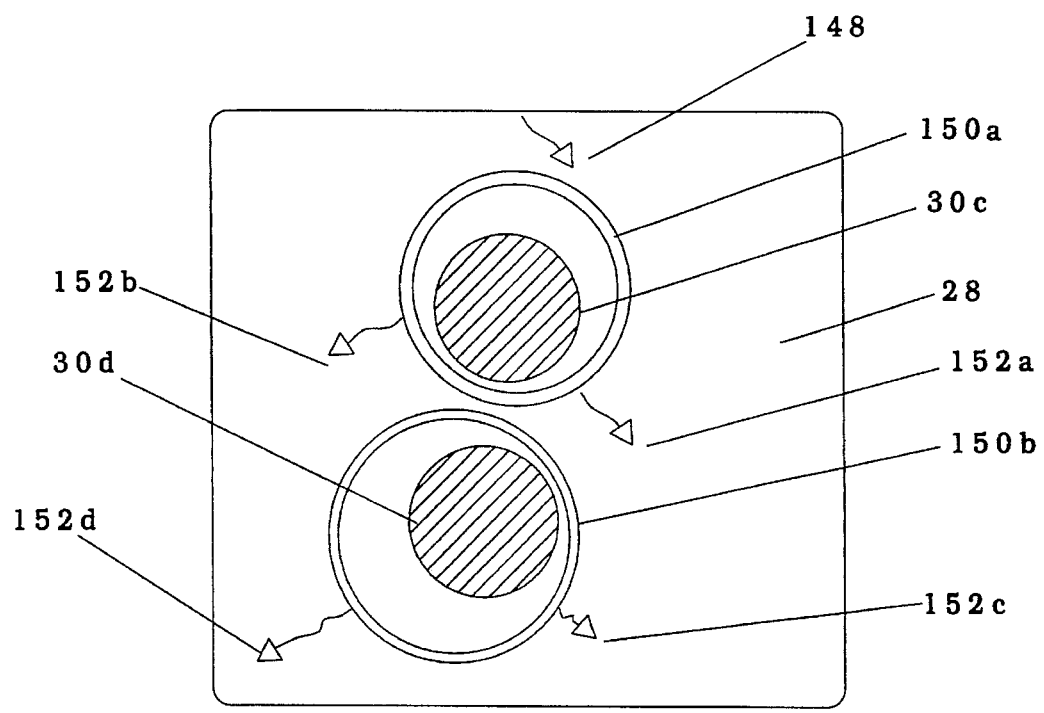
FIG. 22 is a schematic of the circuit shown in FIG. 3 encircled by two conductive helix embodiments.

FIG. 13 shows a perspective view of a cage structure 100 that acts as a number of stakes 92 shown in FIG. 22 would to surround the arrhythmogenic site with a single insertion. Cage 100 has a plurality of stakes 102a, 102b, 102c, and 102d branching out from a center 104 such that the sharp ends 106 of each stake may pierce the heart muscle with ease. One or more stakes, such as 102d, has a barb 108 on the end to prevent the stake from disengaging after it has been inserted into the heart muscle. Again, cage 100 would be advanced from the lumen of a catheter by a controlling stylet. Engagement techniques such as recessed balls 74 in FIG. 9 shown engaging elliptical region 64 of head 54 connected to helix 46 could be used. Hole 112 could have single or double threads for alternate connection mechanisms. If so desired, the cage ends 106 could be angled in as shown in FIG. 13 towards the axis of symmetry such that deformation of stakes 102a, 102b, 102c, and 102d would result upon insertion into the heart muscle causing cage legs 102a, 102b, 102c, and 102d to become closer.

Figure 14:
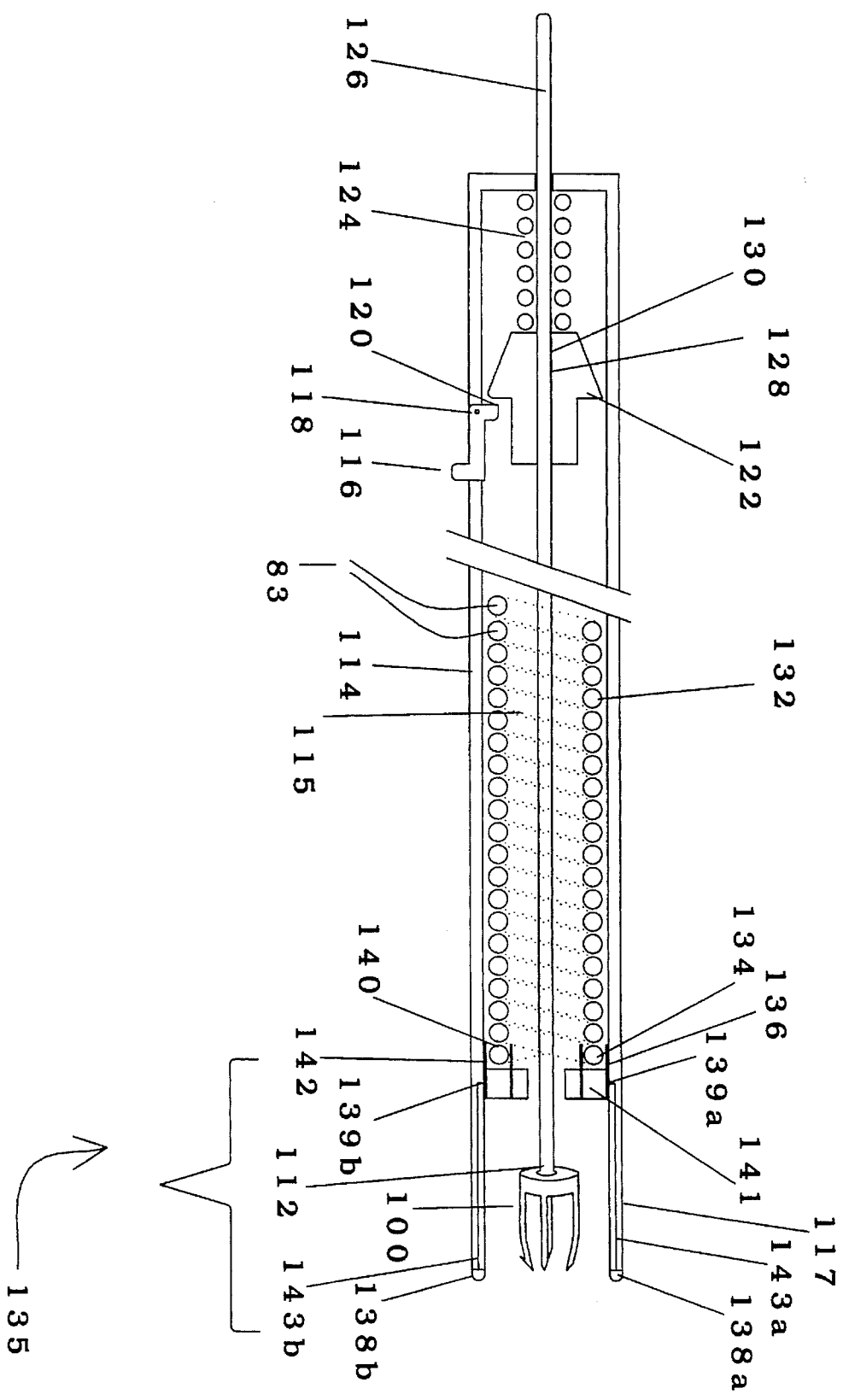
FIG. 14 is a section view of a delivery catheter for stake or cage implantation.

FIG. 14 shows a sectional view of a delivery catheter for either the stake embodiment shown in FIG. 12 or the cage embodiment shown in FIG. 13. The embodiments of the implanted device shown in FIG. 12 and FIG. 13 have the same requirements from a delivery catheter in that it must use sufficient force over a controlled displacement to insert the device. Delivery catheters such as shown in FIG. 14 would be of different diameters for different embodiments of the implanted devices. Cage 100 is shown threaded on to the end of central shaft 126 which traverses the entire length of the delivery catheter. Threaded over stylet male threads 128 in a proximal region is a stylet catch 122 that catches on catheter catch 120 when the spring 124 is compressed and the release 116 is engaged with stylet catch 122 preventing transmission of the force through center shaft 126 to distal cage 100 for insertion into the heart wall. Cage 100 could just as well be a stake as shown in FIG. 12, in that it has the same requirements from a delivery catheter. Center shaft 126 connects to cage 100 by any of the techniques previously discussed. As already mentioned, the state of the art connection means should be used. The distal region of FIG. 14 shows another means for connecting distal electrodes 138a and 138b to the proximal connectors 83. Here a two filar coil 132 runs the length of the delivery catheter inside the lumen 115 of jacket 114 such that the centerline of the separate conductor coils travel a helical path of approximately the same pitch and the same radius. These conductors connect to a distal mapping region 135 in which the conductor transitions from the coiled structure to conductors embedded in the wall of jacket 117. The transition from the two filar coil 132 to the embedded conductors 143a and 143b occurs by crimps 136 and 142 on the ends of the conductor 134 and 140. The crimp structure is embedded in positioning disc 141 which is considered part of distal mapping region 135. Positioning disc 141 acts not only as a means of connecting coiled conductors 134 and 142 to embedded conductors 143a and 143b, but also acts to guide the center shaft 126 into position with the connection mechanism inside of cage 100. Distal mapping region 135 could be assembled prior to attachment to jacket 114 such that it could more easily be crimped to conductor coil 132.

Figure 15:
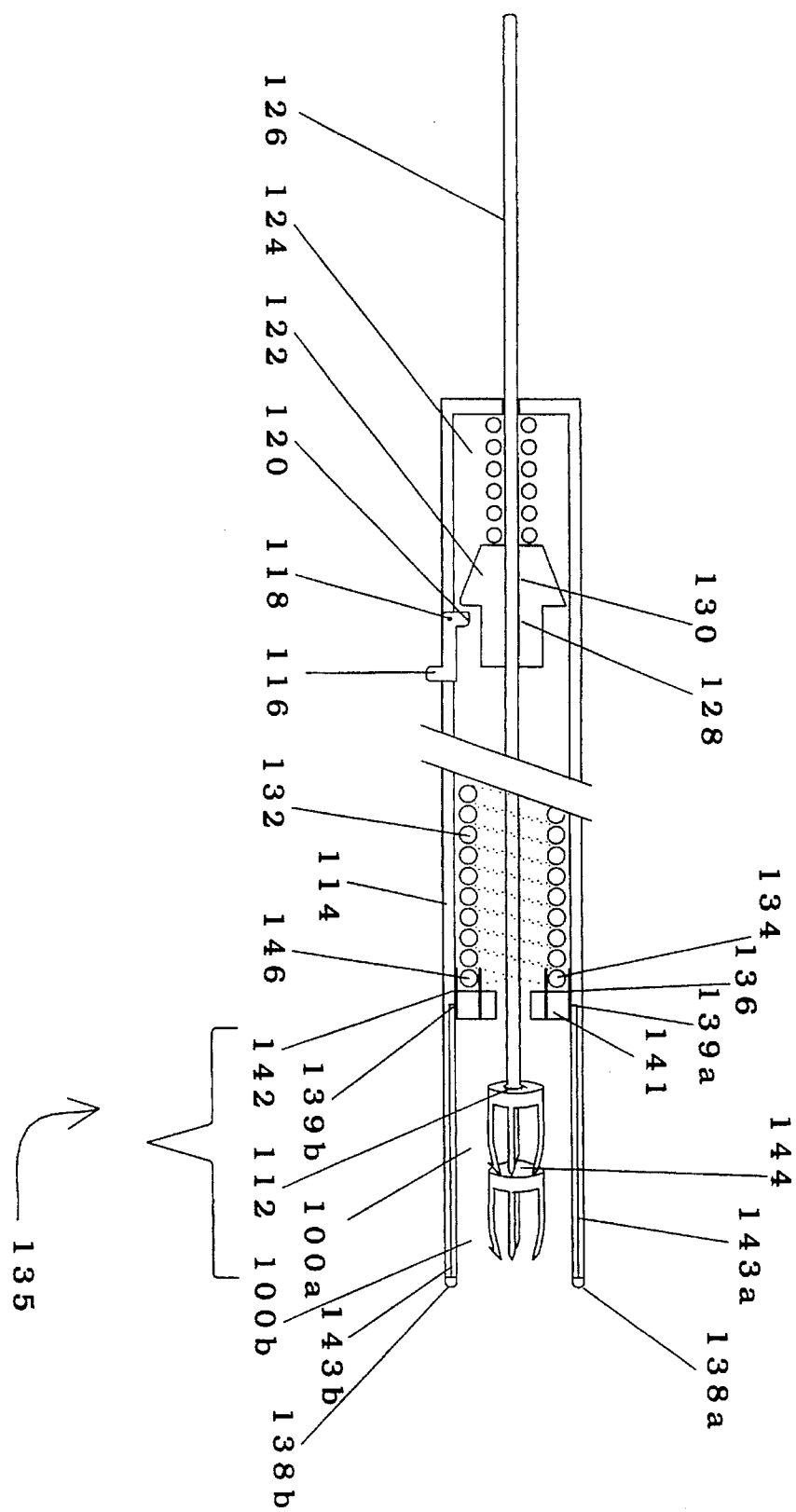
FIG. 15 is a section view of a delivery catheter for multiple stake or cage implantation.

As previously mentioned, a single catheter could be used to insert a number of devices that require sufficient force over a controlled displacement for insertion. FIG. 15 shows a sectional view of such a delivery catheter. This catheter is identical to the catheter shown in FIG. 14 except for two variations. First is the presence of two cage structures 100a and 100b. Cage 100a nestles inside cage 100b such that it can effectively transmit force to cage 100b. A rotating key fit 144 (not shown) exists where the legs of cage 100a must be rotated 180 degrees with respect to cage 100b to obtain disengagement of cage 100a from cage 100b. Such engagement techniques are known to those familiar with the art of mechanical connections. Upon displacement of release 116 such that stylet catch 122 is no longer restrained, sufficient force is transmitted through central shaft 126 to cage 100a to cage 100b which penetrates into the heart wall. Stylet 126 is rotated 180 degrees to disengage cage 100a from cage 100b. The second variation is that center shaft 126 is longer and has male threads along a longer length such that it can be advanced inside female threads 130 in stylet catch 122. Advancing central shaft 126 will result in protrusion of cage 100a from the distal end of the delivery catheter. Once cage 100a is fully protruding from distal end of the delivery catheter, stylet 126 is pulled back such that central catch 122 compresses spring 124. The catheter is then essentially equivalent to the delivery catheter shown in FIG. 15 and cage 100a may be implanted. Although only two cage structures are shown, a similar delivery catheter could be used in which a plurality of stakes or cages would be implanted in a similar manner.

Figure 16:
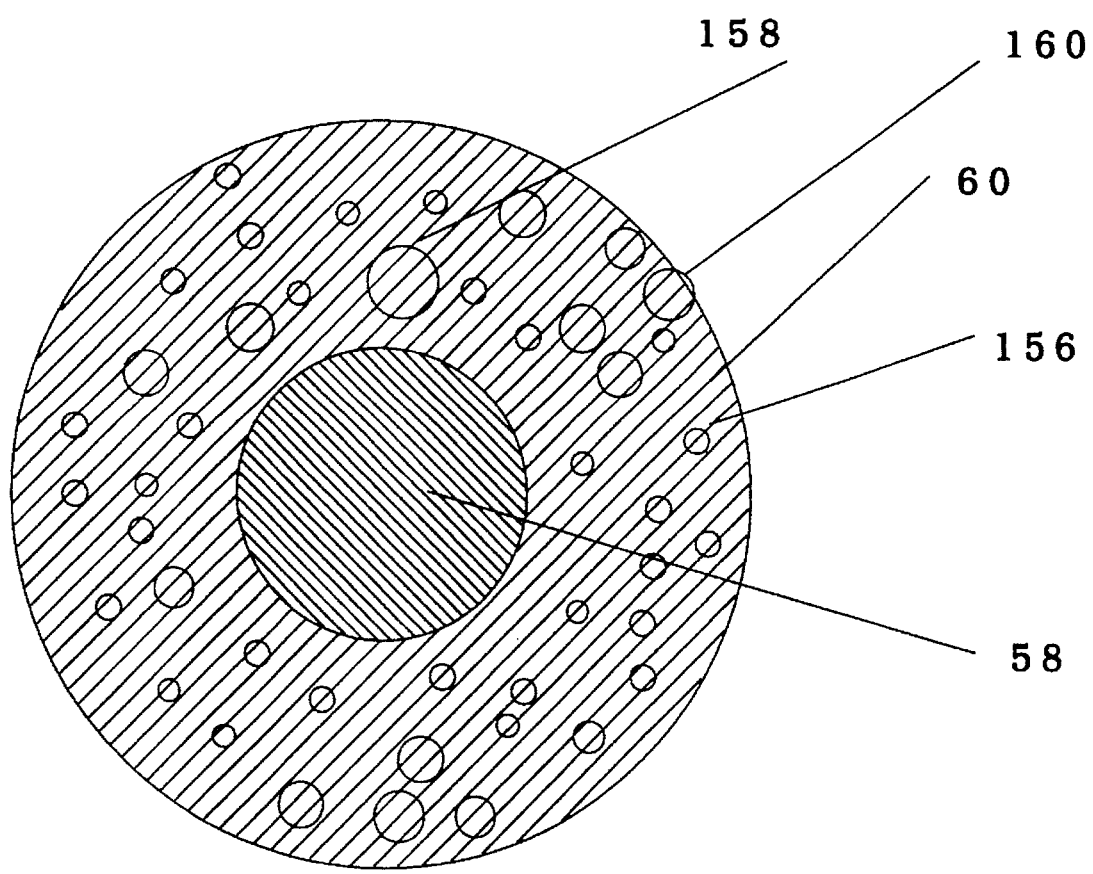
FIG. 16 is a cross section of the device incorporating a controlled release matrix.

FIG. 16 shows a cross sectional view of a circular cross section of a typical cross section of a stake, helix, or cage that has been coated with a polymer release matrix for drug delivery. There is a rigid core 58 covered with a polymer matrix 60. Embedded in the polymer matrix 60 are large particles of the drug 158 and small particles of the drug 156 below the surface of the matrix 60, just as there are particles of the drug at the surface 160. Drugs may be exposed on the surface 160 or they may be fully embedded. There are delivery mechanisms for transporting particulate drugs through the polymer including but not limited to diffusion, osmotic swelling, and biodegradation of the polymer.

Figure 17:
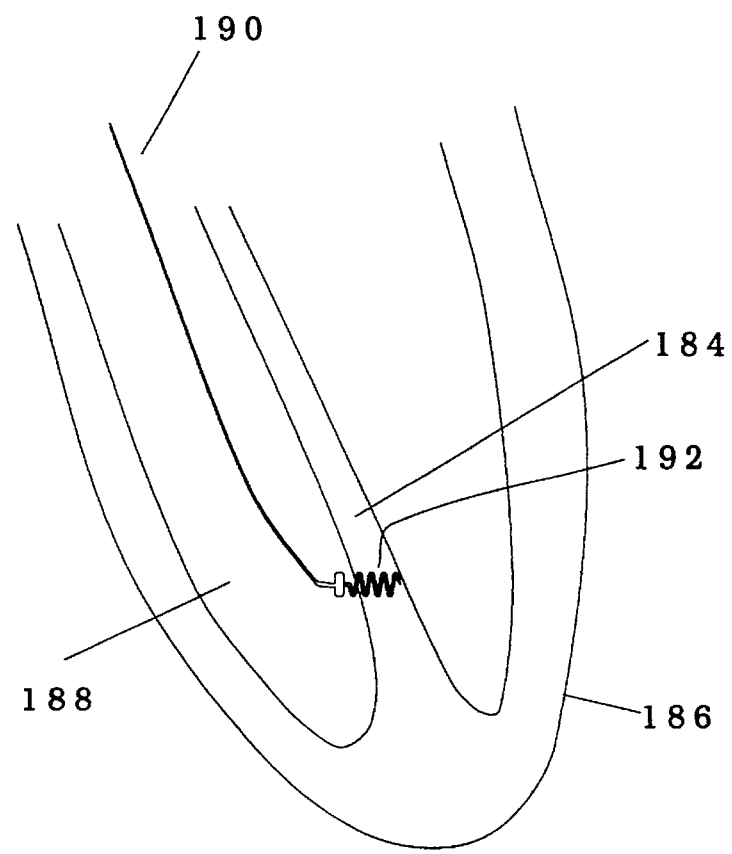
FIG. 17 shows a helix device with an attached tube for repetitive drug delivery.

FIG. 17 shows a sectional view of a helix embodiment 192 implanted in the septum 184 of the heart 186 and connected at the head to a catheter 190. Helix 192 has been guided into the right ventricle via the subclavian vein. Catheter 190 comes loose from another embodiment of the delivery catheter and connects on its proximal end to a delivery port such as Johnson and Johnson's Infusaport™ for continuing local drug therapy. A patient may then administer therapy into a subcutaneous reservoir essentially recharging the concentration of the drug in the polymer release matrix.

Figure 18:
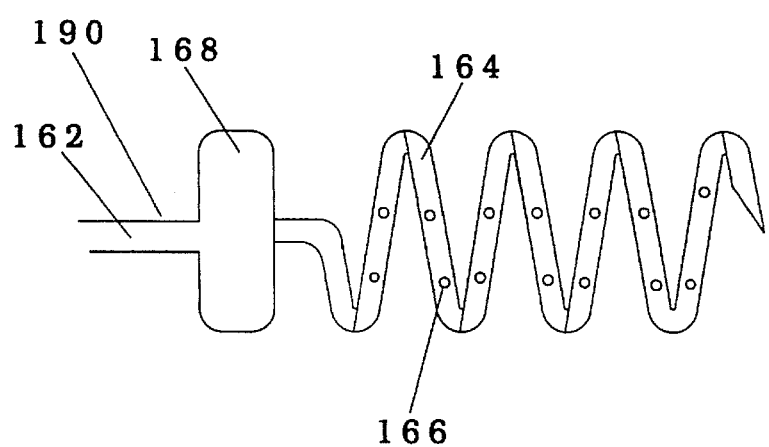
FIG. 18 shows a perspective view of a hollow helix with apertures

FIG. 18 shows another embodiment in which the device has a hollow core with apertures that will allow migration of fluids from the delivery catheter. Catheter 190 is connected to head 168 of hollow helix 164 such that drugs can pass through catheter 190 into helix 164. Helix 164 has a plurality of apertures 166 that allow a drug to migrate into the myocardium. Catheter 190 would loosely fit over the stylets in the various delivery catheters discussed such that it remains in place once the stylet is disengaged from head 168. Once implanted, the catheter 190 is connected on its proximal end to a subcutaneous delivery port which the patient can inject with drugs for continuing local therapy. Drugs can then flow through lumen 162 of catheter 190, through hollow helix 164 and into the tissue via apertures 166.

Materials

These various embodiments may be made from essentially any single biocompatible material or combination of materials such that all materials exposed to the patients body are biocompatible. Although the preferred embodiment is a structure made entirely of biocompatible materials, many biocompatible materials may be used to cover, coat, or clad a non biocompatible material to isolate it from interactions with the patient.

Although there are many issues in selecting the appropriate material for a given application, after biocompatibility the electrical characteristics are of primary importance. Insulative materials will all tend to have similar effects; conductive materials will have less similar effects. Materials such as platinum, gold, elgiloy, titanium, MP35N, Stainless Steel, and other metallic biocompatible conductors have different electrical conductivities and electrochemical interfacial characteristics.

The electrochemical interfacial characteristics are those that govern charge transfer across a metal structure in an electrolyte and have been thoroughly studied. [Mansfield, Peter: Myocardial Stimulation: the electrochemistry of electrode tissue coupling, Am. J. of Physiology Vol. 212, No. 5, May 1967]. By selecting different materials, slightly different electrical characteristics of the different devices can be achieved. By combining electrically insulating materials and electrically conducting materials appropriately, one may tailor a particular embodiment to a particular arrhythmia.

The materials are not limited to those we are currently familiar with, as new alloys and polymers may provide further advantages currently unknown. In addition to the conductors described above, insulative biocompatible materials such as polytetraflouroethylene, expanded polyteraflouroethelyne (EPTFE), polyurethane, silicone, polyester, as well as others may be used.

The nonconductive materials that the device is wholly or partially made of may be controlled release matrices.

Operation of Invention

Through electrical mapping techniques an Electrophysiologist or individual trained in the art of intracardiac catheter placement and electrical mapping procedures identifies the arrhythmogenic site in a patient. Again, types of arrhythmogenic sites include, but are not limited to: accessory atrioventricular pathways, ectopic loci, and reentrant circuits.

The arrhythmogenic site may be identified with techniques known in the art of cardiac electrophysiology. The arrhythmogenic site may be located using an expandable multipolar catheter mapping system such as disclosed in U.S. Pat. No. 5,239,999, a standard cylindrical quadripolar mapping catheter, or even the delivery catheters disclosed here in FIG. 9, FIG. 14 or FIG. 15. Once identified, the device is placed in the myocardium in the region of the arrhythmogenic site such that the local potential gradients and electric fields in this region are modified to remove or reduce the disturbance introduced by the arrhythmogenic site.

If the device is implanted with delivery catheter as shown in FIG. 9, electrical mapping may be performed as the structure is inserted into the heart wall using the a portion of the device such as tip 79 as an electrode. The engaged inner stylet 72 will allow torque to be delivered to the helix 46 from a proximal knob 78 which can be rotated by hand by the implanting physician. Other embodiments could include motorized insertion techniques. The helix would be advanced out the end of the catheter and into the heart wall. Electrodes 77 and 81 may be used to ascertain that the distal portion of the catheter is in contact with the electrically active heart wall and that the advanced helix is therefore successfully inserted into the heart wall.

The catheter delivery system shown in FIG. 14 could also be used to perform mapping prior to and during insertion into the heart wall of the cage or stake embodiment of the device. Distal mapping electrodes 138a and 138b shown in FIG. 14 may be used to precisely locate the site for implantation. Once located, the physician would release catch 116 such that the stylet catch 122 is pushed forward by compressed spring 124 and the cage 100 or stake (not shown) would be inserted into the region of the heart chosen for implantation. Mapping electrodes 138a and 138b could be used to stimulate the heart with low amplitude pulses in a region of interest to determine if an arrhythmia can be induced, just as they may be used to measure appropriate characteristics of the patients electrophysiology. After insertion of the structure, tests could be performed prior to disengagement to determine if the site chosen is appropriate. If appropriate, connecting stylet 126 would be disengaged. If inappropriate, the implanted device could be removed by applying force to stylet 126. If the need to remove the structure occurs often, other embodiment of these devices do not include barb 108 in FIG. 13 or barb 96 in FIG. 12.

FIG. 15 shows another delivery catheter that is very similar to that shown in FIG. 14. Here, the physician would implant distal cage 100b or stake (not shown) into the heart and proceed as he would proceed with delivery catheter 14. A second cage 100a could be introduced after the first is disengaged by advancing the stylet 126 inside the stylet catch 122 and then pulling back on stylet 126 to compress spring 124 until stylet catch 122 can be secured with catheter catch 120. Delivery is then identical to that of catheter shown in FIG. 14.

Some of the embodiments of this device such as the helix geometry, allow the physician or individual trained in the art, the option of performing some evaluative techniques before disengaging the catheter from the implantable device. These evaluative techniques may consist of mapping in the region of the arrhythmogenic site, determining if the arrhythmia is inducible by electrical means, or other tests.

If the procedure is determined to be successful, the catheter is disengaged from the device, which is left permanently implanted in the heart wall, and the procedure may be terminated. A plurality of devices may be implanted at a single arrhythmogenic site, and if a plurality of regions are suspected of contributing to the arrhythmia, a plurality of devices may be implanted at a plurality of locations within the heart. If the procedure is deemed to be unsuccessful, the physician has the option of disengaging the device from the catheter and inserting another device in the region or removing the device and repositioning it. Inserting the device, performing tests, and removing the device may provide information currently not available to the implanting physician.

Theory of Operation

This device is believed to operate by acting as either an electrically insulative barrier to an electrical signal, a capacitively coupled short across the region of tissue in question, an averager that reduces the effective signal of the myocardial region in question, or any combination of these mechanisms. Each of these specific mechanisms will be discussed in turn.

Figure 4:
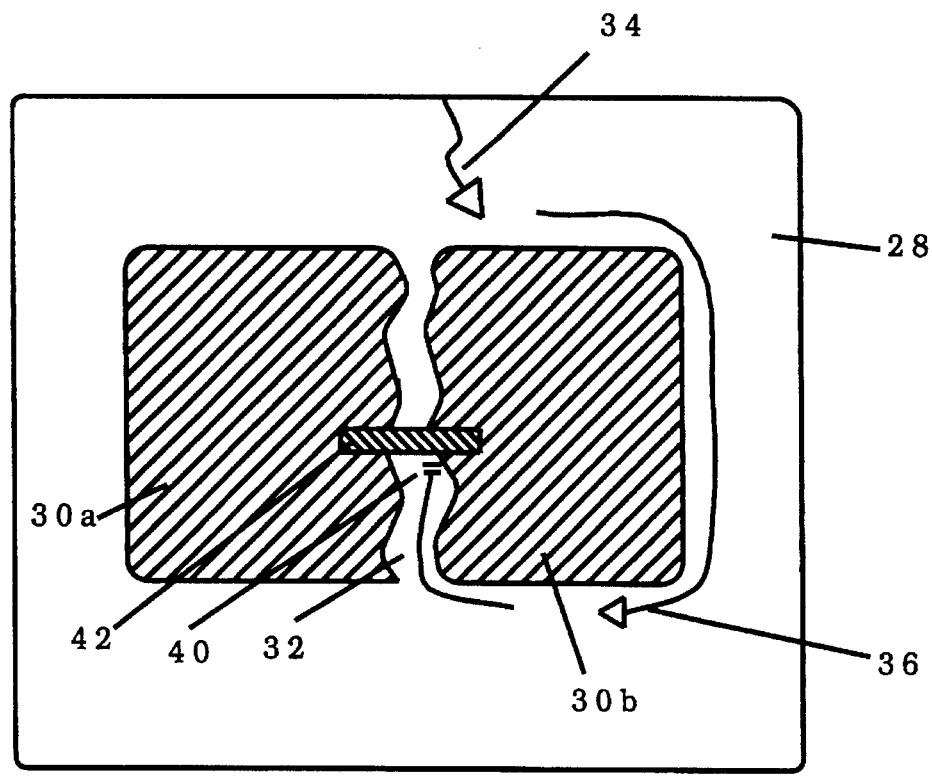
FIG. 4 is a schematic of the circuit in FIG. 1 after a successful ablation procedure.
Figure 5:
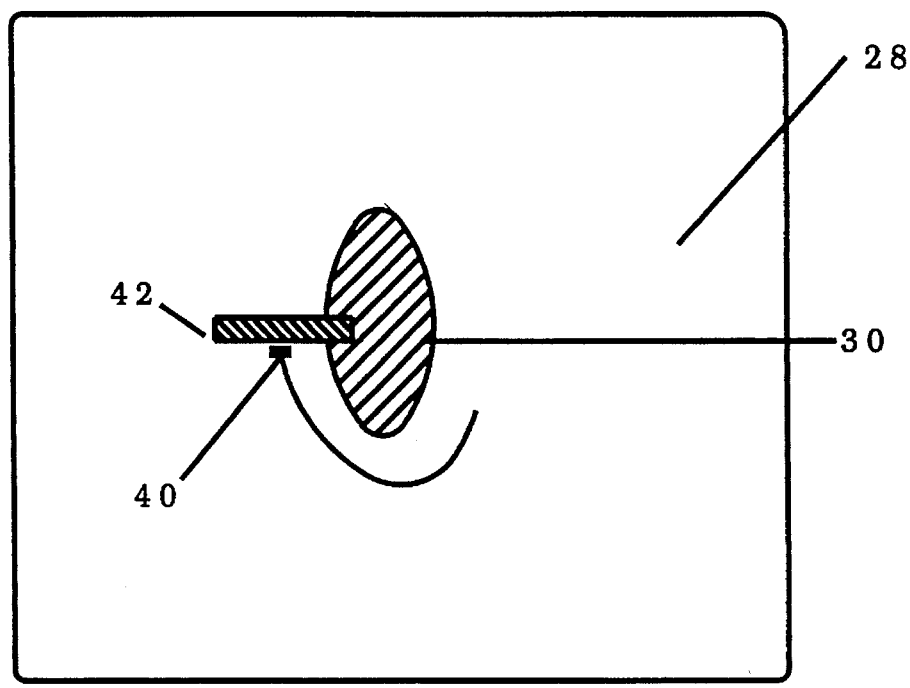
FIG. 5 is a schematic of the circuit in FIG. 2 after a successful ablation procedure.
Figure 6:
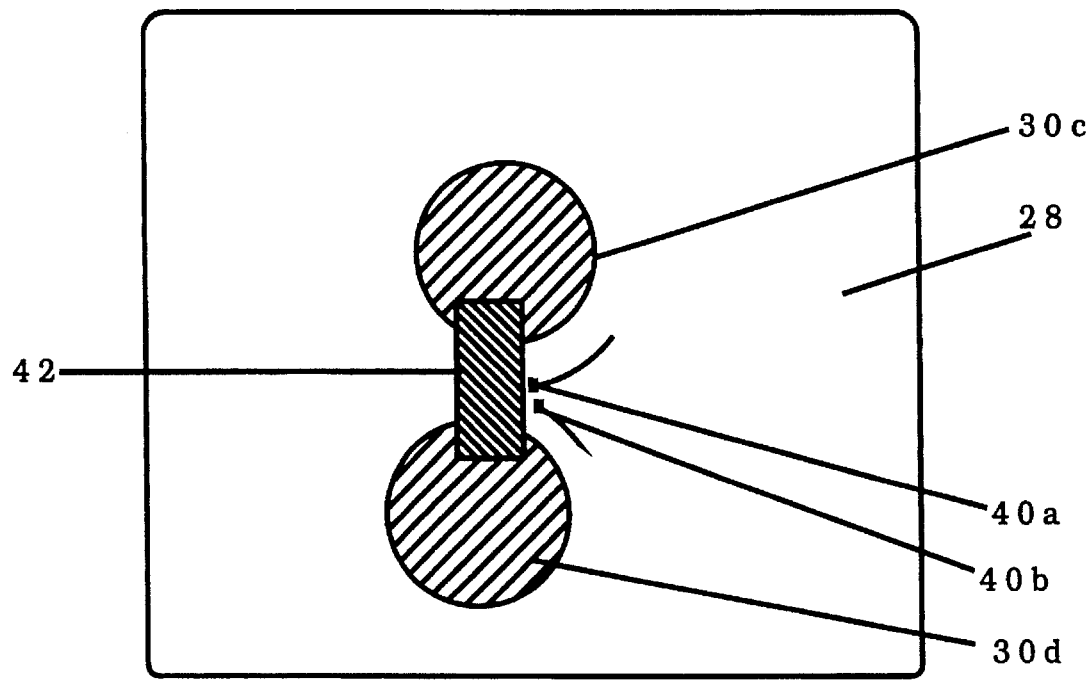
FIG. 6 is a schematic of the circuit in FIG. 3 after a successful ablation procedure.

A nonconductive embodiment of any of the different possible geometries of the device will act as an insulative barrier preventing conduction through the device, and acting much as a region of necrotic tissue that is created by ablation. There is one fundamental difference: the device disclosed here does not change the cellular conductivity locally by destroying tissue, but rather displaces the cells spatially introducing an insulating structure in the region. If the structure of the device separates the region of tissue in which there is problematic conduction, it will function as an insulative barrier preventing propagation as shown in FIGS. 4, 5, and 6. However, the nonconducting barrier created in the myocardium by the device has many advantages over the nonconducting barrier created by destroying myocardial tissue through ablation. The device may be implanted beside a suspected arrhythmogenic site, or in the case of the helix embodiment, may actually surround the arrhythmogenic site. Prior to insertion of a selected device, the geometry required for a given arrhythmogenic site will be selected. Because the geometry is given before implantation, the procedure will be much more repeatable than existing ablation techniques. In addition, the nonconducting barrier may be introduced at a depth within the heart wall that cannot be treated with ablation. In addition, the nonconducting barrier may be removed if desired with only moderate tissue damage and is therefore a more reversible procedure. In addition, the nonconductive embodiment may serve as a substrate for local controlled drug release of a number of beneficial pharmacological agents.

Figure 19:
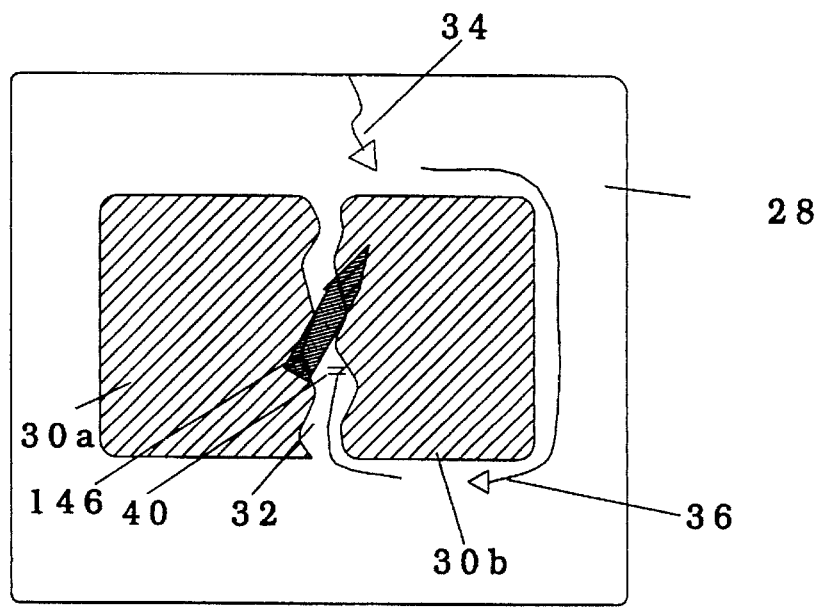
FIG. 19 is a schematic of the circuit in FIG. 1 disrupted by the stake of FIG. 12.

FIG. 19 shows a nonconductive stake interrupting the circuit previously described in FIG. 1. Much like the ablated region 42 in FIG. 4, stake 146 introduces an interruption to the circuit 40 preventing reentry.

The conductive embodiments of the device will act as a short across the region of the arrhythmogenic site. By electrically connecting the tissue around the arrhythmogenic site, the myocardial currents jump over the problematic region of the arrhythmogenic site. Cells on either side of a conductive device will be coupled capacitively to the device and therefore to each other.

Metals are very efficient conductors of electrons, but not for ions. On the other hand, aqueous electrolyte solutions are ionic conductors and are hostile to electrons. Consequently, at the interface between a metal and an aqueous electrolyte solution, there is a mismatch in the type of charge carrier used. In the absence of a chemical mechanism to convert one type of charge into the other, the interface behaves as a capacitance: a change in the electronic charge density on the metal side is accompanied by a compensating change in ionic charge density on the solution side, so that electroneutrality is maintained. The two types of charges can come very close to each other spatially without the possibility of neutralizing each other. This gives rise to an interfacial capacitance. [deLevie, Robert: The Admittance of the Interface between a Metal Electrode and an Aqueous Electrolyte Solution: Some Problems and Pitfalls, pp337–347 Annals of Biomedical Engineering, Special Issue]. Typically the interface between a metal and tissue is modeled as a resistor and a capacitor in parallel; at low currents the impedance associated with the capacitive leg of the circuit is small and the impedance associated with the resistive leg is large. Different biocompatible metals such as Platinum Iridium Alloys, MP35N, Titanium, and Stainless Steels may be selected for different capacitive and resistive effects.

Figure 20:
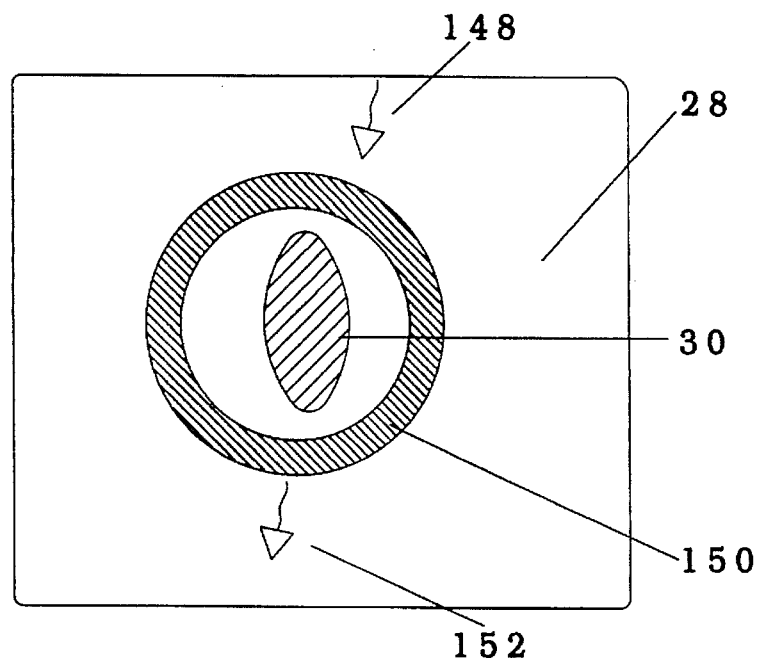
FIG. 20 is a schematic of the circuit in FIG. 2 encircled by a conductive helix embodiment.
Figure 21:
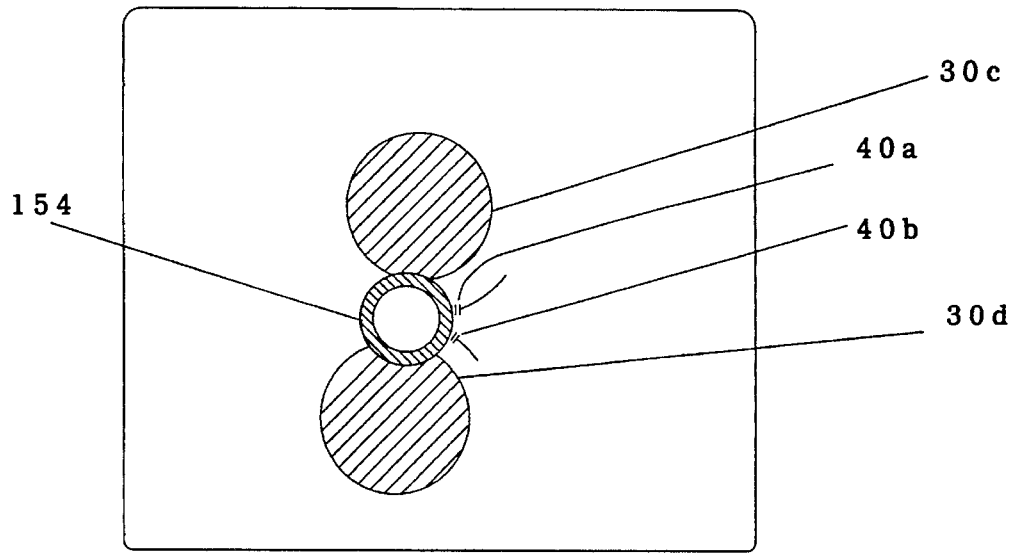
FIG. 21 is the schematic of the circuit in FIG. 3 disrupted by a non conductive helix embodiment.

Because the currents are very small, charge transport from a cardiac cell on one side of the device to a cardiac cell on the other side of the conductive device is likely to occur by capacitive coupling. Such a functionality is portrayed in FIGS. 20 and 22. In FIG. 20, a signal 148 jumps across the arrhythmogenic site 30 via capacitive coupling of the normal heart cells 28 to the conductive structure 150 on one side of the arrhythmogenic site to the cells on the other. The signal 152 continues on the far side of the necrotic arrhythmogenic site 30 and the necrotic arrhythmogenic site 30 is essentially bypassed. Similarly, in FIG. 22, a signal 148 jumps across a first necrotic arrhythmogenic site 30c via capacitive coupling of the normal heart cells 28 to a first conductive structure 150a on one side of the arrhythmogenic site to the cells on the other. The signal 152a continues on the far side of the necrotic arrhythmogenic site 30c and the necrotic arrhythmogenic site 30c is essentially bypassed. This is then repeated with conductive structure 152b acting to carry the signal through necrotic arrhythmogenic site 30d. Signals 152c and 152d indicate the bypassing of arrhythmogenic site 30d. Coating of the implanted device with materials such as titanium oxide, platinum black, or even sintered platinum balls to augment the surface area and improve tissue to device capacitive coupling is also an option and not new to those familiar with the art of cardiac stimulation. (Stokes, K.; Bornzin, Gene: The Electrode-Biointerface: Stimulation, Chapter 3 in Modern Cardiac Pacing edited by Serge Barold, Mount Kisko, N.Y.; Futura Publishing Co., 1985.)

The conductive embodiment of this device provides a means for eliminating an arrhythmia in a manner completely different from the ablation techniques previously discussed, and yet it still retains all of the advantages of the nonconducting barrier embodiment discussed above. Prior to insertion of a selected conductive device, the geometry required for a given arrhythmogenic site will be selected. Because the geometry is given before implantation, the procedure will be much more repeatable than existing ablation techniques. In addition, the conductive device may be introduced at a depth within the heart wall that cannot be treated with ablation. In addition, the conductive device may be removed if desired with only moderate tissue damage and is therefore a more reversible procedure. In addition, the conductive embodiment may serve as a substrate for local controlled drug release of a number of benificial pharmocological agents.

Neither the insulative barrier nor the conductive short embodiments need to completely block or completely jump the arrhythmogenic site to be viable therapies for cardiac arrhythmias. Cardiac cells require a potential increase to a critical level or threshold at their membrane in order to create an action potential. Purkinjje fibers for example require a threshold potential that is around 30 mV above their resting potential. Preventing the cells that contribute to the aberrant pathway from reaching their threshold potentials will result in effective elimination of the action of those cells. If the insulative embodiment of the device does not completely cleave the cellular regions that define a problematic pathway, it is likely that the device will still result in effective interruption of the inappropriate conduction pathway. Insertion of an insulating device will result in a change of the local charge transfer that may be sufficient to prevent the cells from reaching their threshold voltage. An insulative region in a three dimensional conductive material will result in a change of the local charge transfer. For example, if the insulative helix embodiment of the device structure surrounds an arrhythmogenic region, the actual conduction pathway may not be cleaved. Instead, the resistance of the tissue to charge transfer in this region will be increased, and the likelihood of the viability of the circuit will be decreased. The conductive embodiment of the device may work similarly.

The conductive embodiment of the device may act to average out the localized voltage potential in the region of the arrhythmia by capacitively coupling a large number of cells together. The idea here is that cells that contribute to the aberrant pathway will not be able to fire because the charge necessary to raise them from their resting potential will be spread over a larger region of tissue. Again, this means for eliminating an arrhythmia is completely different from the ablation techniques previously discussed, and yet it still retains all of the advantages of the nonconducting barrier embodiment discussed above.

While I believe that this implantable device will function in the manner described, I do not wish to be limited by this.

Conclusions, Ramifications and scope of Invention

Thus the reader will see that the different embodiments of the invention provide a means to effectively electrically eliminate a known region of cardiac tissue from the electrical action of the heart. The device has the great advantage of not causing unnecessary tissue damage and in certain embodiments is easily removed or repositioned. This second advantage allows physicians to perform evaluative tests. Prior to insertion of a selected device, the geometry required for a given arrhythmogenic site will be selected. Because the geometry is given before implantation, the procedure will be much more repeatable than existing ablation techniques. In addition, the different embodiments may be introduced at a depth within the heart wall that cannot be treated with ablation. In addition, the nonconductive embodiment may serve as a substrate for local controlled drug release of a number of beneficial pharmacological agents.

While my above description contains many specificities, these should not be construed as limitations on the scope of the invention, but rather as an exemplification of one preferred embodiment thereof. Many other variations are possible. For example, a thread or suture of conductive or non conductive material could be stitched or sewn around the arrhythmogenic site with an appropriate delivery catheter, the devices could be implanted through a trocar through the chest such that the device enters the heart epicardially, and the device could be made from as yet unidentified biocompatible materials. Other examples include a cage structure that would be inserted by a sharp delivery catheter into the heart wall and pulled back after the jacket of the delivery catheter was removed, or a jointed wire or ribbon that can be advanced from a catheter delivery system such that it closes again on itself. Accordingly, the scope of the invention should be determined not by the embodiments illustrated, but by the appended claims and their legal equivalents.

I claim:

1. A medical device implantable in a heart, for treating arrhythmogenic sites in the heart, the device comprising:
   a electrically inactive structure having an exposed surface and biocompatible at least over the exposed surface, said structure adapted to be chronically implanted into cardiac tissue within a region substantially adjacent to an arrhythmogenic site in a heart, and, when so implanted, altering conduction properties of the cardiac tissue within said region; and
   wherein the structure incorporates a coupling means for releasably coupling the structure to a delivery device operable to deliver the structure to the region and implant the structure into the cardiac tissue, said coupling means operable to enable disengagement and removal of the delivery device after the structure is implanted.

2. The device of claim 1 wherein:
said structure is selected from a group consisting of helical bodies, stakes, and cages.

3. The device of claim 1 wherein:
said structure is formed of biocompatible materials selected from the group consisting of polytetrafluoroethylene, expanded polytetrafluoroethylene, polyester, polyurethane, silicon, platinum, iridium, titanium, and MP35N.

4. The device of claim 1 wherein:
said structure, at least over an outermost portion thereof that includes said exposed surface, is constructed of a biocompatible material selected from the group consisting of platinum black, titanium nitride, sintered platinum, roughened platinum, roughened MP35N, and roughened titanium, whereby the effective surface area of the structure is enhanced to augment electrical coupling of the structure and the cardiac tissue.

5. The device of claim 1 further including:
a delivery catheter releasably coupled at a distal end thereof to said structure by said coupling means, adapted for intravascularly delivering the structure into the heart and to said region, and further operable at a proximal end thereof to at least partially embed the structure within said cardiac tissue at said region.

6. The device of claim 1 wherein:
said structure includes means for delivering a predetermined pharmacological agent to said cardiac tissue at said region, for further altering conduction properties of said tissue within said region.

7. The device of claim 6 wherein:
said structure includes a substrate coated with a non-conductive controlled release matrix less rigid than the substrate, with the controlled release matrix being at least partially embedded within said tissue when the structure is so implanted.

8. The device of claim 6 wherein:
said predetermined pharmacological agent is selected from a group consisting of anti-arrhythmic agents, angiogenic growth factors, anti-inflammatory agents, and their combinations.

9. The device of claim 6 wherein:
said structure includes a rigid core material forming a proximal head and a distal tip, and an insulative controlled release matrix covering the rigid core material between the head and the tip, to facilitate use of the structure for electrical mapping of said tissue when the structure is at least partially embedded into the tissue.

10. The device of claim 1 wherein:
said structure includes a hollow core and a plurality of apertures from the hollow core open to the outer surface of the structure, a proximally located head in fluid communication with the hollow core, and a tube coupled to the head for supplying a pharmacological agent to the hollow core via the head.

11. The device of claim 10 wherein:
said structure further includes a non-conductive controlled release matrix forming a coating over said apertures, for delivering said predetermined pharmacological agent to an innermost surface of said controlled release matrix.

12. A method of locally altering electrical activity in cardiac tissue at a selected site in the region of the heart, including:
   measuring electrical activity in cardiac tissue, to identify a potential implantation site;
   introducing a first electrically inactive and biocompatible implantable device into the region of the heart, and at least partially embedding said first implantable device into cardiac tissue at the site to effect an implantation.

13. The method of claim 12 further including:
after said implantation, performing a plurality of electrical measurements in cardiac tissue proximate the site and, based on results of said electrical measurements, performing at least one of the following sub-steps:
   (i) determining that the implantation has successfully altered conduction properties as intended;
   (ii) based on a determination that the implantation has not successfully altered conduction properties as intended, removing and repositioning the first implantable device; and
   (iii) responsive to determining that the implantation has not successfully altered conduction properties as intended, embedding a second electrically inactive and biocompatible implantable device proximate the first implantable device and proximate said site.

14. The method of claim 13 further including:

after said performing the plurality of electrical measurements and before performing said at least one substep, supplying a pharmacological agent via the first implantable device to cardiac tissue proximate the first implantable device.

15. The method of claim 13 further including:

after said implantation and before said performing the plurality of electrical measurements, supplying a pharmacological agent via the first implantable device to cardiac tissue proximate the first implantable device.

16. The method of claim 12 further including:

after said implantation of the first implantable device, supplying a pharmacological agent via the first implantable device to cardiac tissue proximate the first implantable device.

17. The method of claim 16 wherein:

said supplying of a pharmacological agent comprises delivering the pharmacological agent from a source to the implantable device via a tube coupled to the implantable device.

18. The method of claim 12 wherein:

said introducing the first implantable device comprises releasably attaching the first implantable device to a distal end of a catheter, using the catheter to intravascularly deliver the device to the implantation site, manipulating the catheter at a proximal end thereof to achieve said implantation, decoupling the catheter from the first implantable device and withdrawing the catheter after said implantation.

19. An apparatus for locally modifying electrical action within a heart, comprising:

an implantable electrically inactive device including tissue penetration means and a coupling means; and a delivery device having a proximal end and a distal end adapted for forming a releasable coupling to said implantable device via the coupling means, adapted for delivering the implantable device to a designated site in a heart and manipulable at said proximal end to implant the implantable device by causing said tissue penetration means to enter tissue; and further adapted for a decoupling from the implantable device and removal after the implantation, whereby the implantable device remains at the site and modifies electrical action at and proximate the site.

20. The apparatus of claim 19 wherein:

said implantable device comprises a means to deliver pharmacological agents to cardiac tissue at and proximate the site.

21. An apparatus for locally modifying electrical action within a heart, comprising:

a biocompatible, electrically inactive, implantable device including a means for penetrating cardiac tissue to effect an implantation of the implantable device at a designated site in a heart, to modify electrical action in the cardiac tissue at and proximate the site.

22. The apparatus of claim 21 wherein:

the implantable device includes a non-conductive controlled release matrix for supplying a predetermined pharmacological agent to the cardiac tissue.

23. The apparatus of claim 21 wherein:

the implantable device, at least over an outermost portion thereof that includes an exposed surface, is constructed of a biocompatible material selected from the group consisting of platinum black, titanium nitride, sintered platinum, roughened platinum, roughened MP35N and roughened titanium, to enhance the effective surface area of the exposed surface and thereby augment electrical coupling of the implantable device and the cardiac tissue.

24. The apparatus of claim 21 further including:

a drug delivery catheter coupled to the implantable device for delivering a pharmacological agent to the implantable device, and wherein the implantable device includes a hollow core in fluid communication with the drug delivery catheter and open to an exterior of the implantable device to supply the pharmacological agent from the delivery catheter to the cardiac tissue.

25. The apparatus of claim 21 further including:

a delivery catheter including a catheter distal end region coupled to the implantable device, said delivery catheter operable at a proximal end thereof to effect said implantation; and an electrode means at the catheter distal end for sensing electrical action in the cardiac tissue before said implantation, to facilitate locating the site.

26. The apparatus of claim 25 wherein:

the catheter is releasably coupled to the implantable device to allow a decoupling and withdrawal of the delivery catheter after said implantation.

* * * * *